United States Patent
Ostovic et al.

(10) Patent No.: US 12,297,185 B2
(45) Date of Patent: *May 13, 2025

(54) CRYSTALLINE FORM OF TEGAVIVINT, METHOD OF PREPARATION, AND USE THEREOF

(71) Applicant: Iterion Therapeutics, Inc., Houston, TX (US)

(72) Inventors: Drazen Ostovic, Redwood City, CA (US); Gowri Sukumar, Spring, TX (US)

(73) Assignee: Iterion Therapeutics, Inc., Houston, TX (US)

( * ) Notice: Subject to any disclaimer, the term of this patent is extended or adjusted under 35 U.S.C. 154(b) by 728 days.

This patent is subject to a terminal disclaimer.

(21) Appl. No.: 17/489,684

(22) Filed: Sep. 29, 2021

(65) Prior Publication Data

US 2022/0098173 A1 Mar. 31, 2022

Related U.S. Application Data

(63) Continuation of application No. 17/037,287, filed on Sep. 29, 2020, now Pat. No. 11,136,307.

(51) Int. Cl.
*C07D 401/12* (2006.01)

(52) U.S. Cl.
CPC ........ *C07D 401/12* (2013.01); *C07B 2200/13* (2013.01)

(58) Field of Classification Search
CPC . C07D 401/12; C07D 211/96; C07B 2200/13; A61K 31/445; A61P 35/02; A61P 35/04
See application file for complete search history.

(56) References Cited

U.S. PATENT DOCUMENTS

| 8,129,519 | B2 | 3/2012 | Cholody et al. |
| 11,136,307 | B1 * | 10/2021 | Ostovic ............... C07D 401/12 |
| 2018/0344713 | A1 * | 12/2018 | Han ...................... A61K 9/0078 |
| 2019/0365729 | A1 | 12/2019 | Dykstra et al. |

FOREIGN PATENT DOCUMENTS

| CN | 108314663 A | 7/2018 |
| WO | 2008/140792 A1 | 11/2008 |
| WO | WO-2019099836 A1 * | 5/2019 |
| WO | 2019/232404 A1 | 12/2019 |

OTHER PUBLICATIONS

International Search Report and Written Opinion for corresponding PCT application No. PCT/US2021/052610 mailed Nov. 5, 2021.
Caira, 1998, Crystalline Polymorphism of Organic Compounds, Design of Organic Solids; 198:163-208.
Soldi, 2015, Design, Synthesis and Biological Evaluation of a Series of Anthracene-9, 10-dione Dioxime β-Catenin Pathway Inhibitors, J of Med Chem, 58(15):5854-5862.

* cited by examiner

*Primary Examiner* — Yih-Horng Shiao
*Assistant Examiner* — Hoi Yan Lee
(74) *Attorney, Agent, or Firm* — Brown Rudnick LLP; Adam M. Schoen

(57) ABSTRACT

The present invention relates to crystalline forms of (9E, 10E)-2,7-bis((3,5-dimethylpiperidin-1-yl)sulfonyl)anthracene-9,10-dione dioxime, pharmaceutical compositions comprising the crystalline form, processes for preparing the crystalline form and methods of use therefore.

20 Claims, 23 Drawing Sheets

XRPD Pattern of Form I

DSC and TGA curves of Form I

PLM Image of Form I

XRPD Patterns overlay of Form II preparation

XRPD Patterns overlay of Form III preparation

DSC and TGA curves of Form III

PLM Image of Form III

XRPD Patterns overlay of Form III samples after drying

XRPD Patterns of Form IV samples

DSC and TGA curves of Form IV

DVS profile of Form IV

PLM Image of Form IV

VT-XRPD Profile of Form IV

XRPD Patterns overlay of Form IV sample after VT-XRPD and exposure to ambient conditions XRPD Pattern of Form V XRPD Pattern of Form VI XRPD pattern of amorphous sample mDSC curve of amorphous sample XRPD pattern of solid obtained from slurry competition in water XRPD pattern of solid obtained from slurry competition in ACN/water (1:1, v/v)

XRPD pattern of solid obtained from slurry competition in ACN/water (1:3, v/v)

PSD of Form I milled at 5 °C

PSD of Form I milled at RT

PSD of Form I milled at 60 °C

PSD of Form IV milled at 5 °C

PSD of Form IV milled at RT

PSD of Form IV milled at 60 °C

PLM image of Form I (left panel) and Form IV (right panel)

PLM image of Form I milled at 5 °C

PLM image of Form I milled at RT

PLM image of Form I milled at 60 °C

PLM image of Form IV milled at 5 °C

PLM image of Form IV milled at RT

PLM image of Form IV milled at 60 °C

XRPD patterns overlay of Form I milled at 5 °C

XRPD patterns overlay of Form I milled at RT

XRPD patterns overlay of Form I milled at 60 °C

XRPD patterns overlay of Form IV milled at 5 °C

XRPD patterns overlay of Form IV milled at RT

XRPD patterns overlay of Form IV milled at 60 °C

CRYSTALLINE FORM OF TEGAVIVINT, METHOD OF PREPARATION, AND USE THEREOF

FIELD OF THE INVENTION

The present invention relates to crystalline forms of tegavivint, aka, (9E,10E)-2,7-bis((3,5-dimethylpiperidin-1-yl)sulfonyl)anthracene-9,10-dione dioxime, pharmaceutical compositions comprising the crystalline form, processes for preparing the crystalline form, and methods of use thereof.

BACKGROUND OF THE INVENTION

Cancer is the second leading cause of death in the United States. It presents complex challenges for the development of new therapies. Cancer is characterized by the abnormal growth of malignant cells that have undergone a series of genetic changes that lead to growth of tumor mass and metastatic properties.

Beta-catenin (β-catenin) is part of a complex of proteins that constitute adherens junctions (AJs). AJs are necessary for the creation and maintenance of epithelial cell layers by regulating cell growth and adhesion between cells. β-catenin also anchors the actin cytoskeleton and may be responsible for transmitting the contact inhibition signal that causes cells to stop dividing once the epithelial sheet is complete.

Wnt/β-catenin pathway has been shown to play a role in cancer. Aberrant β-catenin signaling plays an important role in tumorigenesis. In particular, colorectal cancer is estimated to have greater than 80% mutations in the β-catenin pathway, leading to unregulated oncogenic signaling. Aberrant β-catenin signaling has been shown to be involved in various cancer types, including but not limited to, melanoma, breast, lung, colon, liver, gastric, myeloma, multiple myeloma, chronic myelogenous leukemia, chronic lymphocytic leukemia, T-cell non-Hodgkin lymphomas, colorectal and acute myeloid leukemia (AML) cancers. Further, aberrant Wnt/β-catenin signaling has been found in a large number of other disorders, including osteoporosis, osteoarthritis, polycystic kidney disease, diabetes, schizophrenia, vascular disease, cardiac disease, hyperproliferative disorders, neurodegenerative diseases, and fibrotic diseases including but not limited to idiopathic pulmonary fibrosis (IPF), Dupuytren's contracture, Nonalcoholic steatohepatitis (NASH), and others. Myeloproliferative neoplasms (MPNs) are a closely related group of hematological malignancies in which the bone marrow cells that produce the body's blood cells develop and function abnormally. The three main myeloproliferative neoplasms are Polycythemia Vera (PV), Essential Thrombocythemia (ET) and Primary Myelofibrosis (PMF). A gene mutation in JAK2 is present in most PV patients and 50% of ET and PMF patients. The beta catenin pathway is activated in MPN in many cases and required for survival of these cells.

Tegavivint and related compounds are described, for example, in U.S. Pat. No. 8,129,519. Tegavivint has the following structural formula:

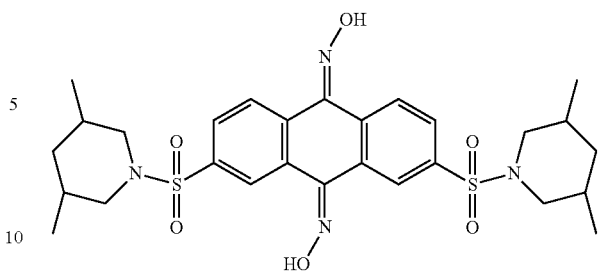

The chemical name is (9E,10E)-2,7-bis((3,5-dimethylpiperidin-1-yl)sulfonyl)anthracene-9,10-dione dioxime The molecular formula of tegavivint is $C_{28}H_{36}N_4O_6S_2$.

The molecular mass of tegavivint is 588.20763 amu.

The small scale chemical synthesis of tegavivint had been disclosed in U.S. Pat. No. 8,129,519. The drug substance/Active Pharmaceutical Ingredient (API) has good chemical and physical stability. However, there is a major concern about physical stability of nanoparticle formulations of tegavivint over time that can manifest as crystal growth (Oswald ripening), or a polymorphic change, which can result in the increase in large particle count, or in generation of unfavorable particle morphology during long term storage of the formulated drug. Thus, there remains a need to perform crystal investigation to explore suitable/relevant polymorph(s) of tegavivint that would be feasible for milling and formulation development to yield a formulation with good long term physical stability. The present invention advantageously addresses this need.

SUMMARY OF THE INVENTION

The present application discloses an invention to address the foregoing challenges and need by providing a crystalline single polymorphic form of tegavivint, referred to throughout this application as Form IV. The current formulation of tegavivint is a nanosuspension created utilizing a milling process. While Form I (BC-2059 obtained from chemical synthesis as is) has been currently utilized as the starting material for the milling process and the end product obtained from milling is nanosuspension of Form I. However, the inventors of present invention have unexpectedly found that there are specific advantages of utilizing Form IV (in comparison to Form I) as the starting material for the milling process to prepare a nanosuspension of tegavivint.

The main advantage is that Form IV is sufficiently unstable so that Form IV gets converted to Form I when milled at an elevated temperature (60° C.). Thus, the system will undergo a full solvent-mediated recrystallization from Form IV to Form I. The crystals for Form I will grow "bottom-up" as they are milled, so the chance of getting any unmilled larger crystals would be significantly diminished. In other words, it is beneficial to utilize Form IV as the starting material because it will eventually be converted to Form I and the only Form I crystals would come from re-crystallization from Form IV. Thus, facilitating suspension with a single polymorph form generated through milling at elevated temperatures would in turn enhance the stability of the suspension.

Thus, in one embodiment, the invention provides a crystalline form of tegavivint, referred to as Form IV which has an X-ray powder diffraction pattern (XRPD) comprising diffraction peaks having °2θ angles selected from the group consisting of 5.0+−0.2°; 7.5+−0.2°; 7.7+−0.2°; 10.2+−0.2°;

14.8+−0.2°; 15.2+−0.2°; 15.4+−0.2°; 18.0+−0.2°; 20.0+−0.2°; 20.5+−0.2°; and 22.2+−0.2°.

In one embodiment, Form IV can be a single crystal.

In one embodiment, Form IV is a trihydrate.

In another embodiment, Form IV has an endothermic peak at about 115.9° C.

In another embodiment, Form IV has an onset of exothermic peak at about 147.1° C.

In yet another embodiment, exothermic decomposition of Form IV starts at about 280° C.

In yet another embodiment, the invention provides a nanosuspension of tegavivint wherein the nanosuspension was prepared by a process comprising using Form IV as the starting material and milling Form IV at a temperature of between about 40° C. and about 60° C., most preferably at about 60° C.

In one embodiment, if the milling process is done at temperature of less than about 60° C., the nanosuspension has to further undergo the annealing process at or above 60° C.

In another embodiment of the invention, pharmaceutical compositions are provided for use in the methods comprising stable nanosuspensions of Form I prepared using Form IV as the starting material, and pharmaceutically acceptable excipient.

In another embodiment of the invention, provided herein are methods for preventing, treating or ameliorating cancer or tumor metastasis in a mammal in need thereof comprising administering to said mammal an effective amount of the compositions of the invention.

DETAILED DESCRIPTION OF THE INVENTION

The present invention relates to crystalline forms of tegavivint. In particular, the present invention relates to a crystalline form designated Form IV of tegavivint, pharmaceutical compositions comprising the crystalline form, processes for preparing the crystalline form and methods of use thereof.

In one embodiment, the crystalline form of tegavivint is designated as Form IV, which has an X-ray powder diffraction pattern (XRPD) comprising diffraction peaks having °2θ angle values independently selected from the group consisting of 5.0+−0.2°; 7.5+−0.2°; 14.8+−0.2°; 15.2+−0.2°; 15.4+−0.2°; 20.0+−0.2°; and 22.2+−0.2°.

In one embodiment, Form IV has an XRPD comprising diffraction peaks having °2θ angle values independently selected from the group consisting of 5.0+−0.2°; 7.5+−0.2°; 7.7+−0.2°; 14.8+−0.2°; 15.2+−0.2°; 15.4+−0.2°; 20.0+−0.2°; and 22.2+−0.2°.

In one embodiment, Form IV has an XRPD comprising diffraction peaks having °2θ angle values independently selected from the group consisting of 5.0+−0.2°; 7.5+−0.2°; 7.7+−0.2°; 10.2+−0.2°; 14.8+−0.2°; 15.2+−0.2°; 15.4+−0.2°; 20.0+−0.2°; and 22.2+−0.2°.

In another embodiment, Form IV has an XRPD comprising diffraction peaks having °2θ angle values independently selected from the group consisting of 5.0+−0.2°; 7.5+−0.2°; 7.7+−0.2°; 10.2+−0.2°; 14.8+−0.2°; 15.2+−0.2°; 15.4+−0.2°; 18.0+−0.2°; 20.0+−0.2°; and 22.2+−0.2°.

In another embodiment, Form IV has an XRPD comprising diffraction peaks having °2θ angle values independently selected from the group consisting of 5.0+−0.2°; 7.5+−0.2°; 7.7+−0.2°; 10.2+−0.2°; 14.8+−0.2°; 15.2+−0.2°; 15.4+−0.2°; 18.0+−0.2°; 20.0+−0.2°; 20.5+−0.2°; and 22.2+−0.2°.

Figure 9A:
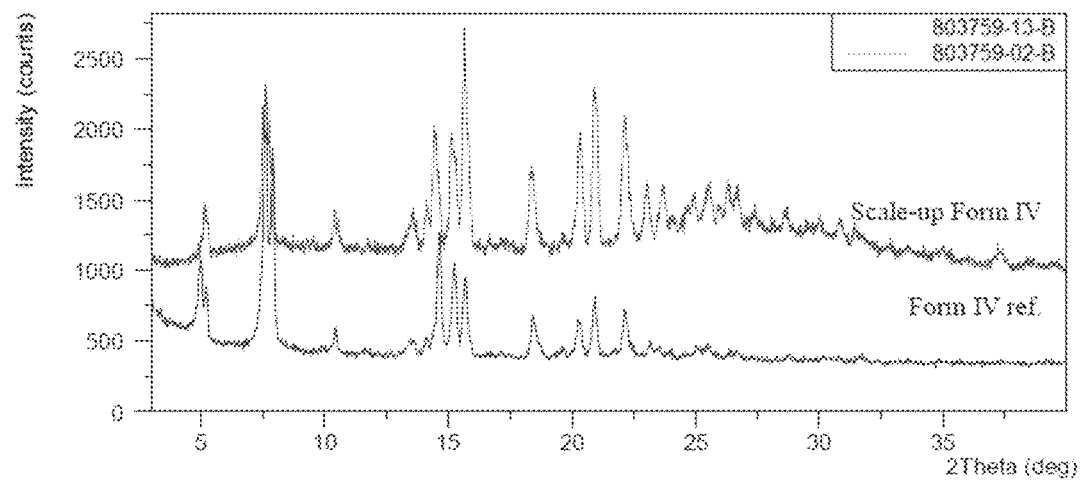
FIG. 9A shows XRPD patterns of Form IV samples.

In another embodiment, Form IV has an XRPD pattern substantially as shown in FIG. 9A.

In another embodiment, Form IV is characterized by having an endotherm with a peak maximum at approximately 115.9° C. by differential scanning calorimetry (DSC).

In another embodiment, Form IV is characterized by having an onset of exothermic peak at approximately 147.1° C. by DSC.

Figure 9B:
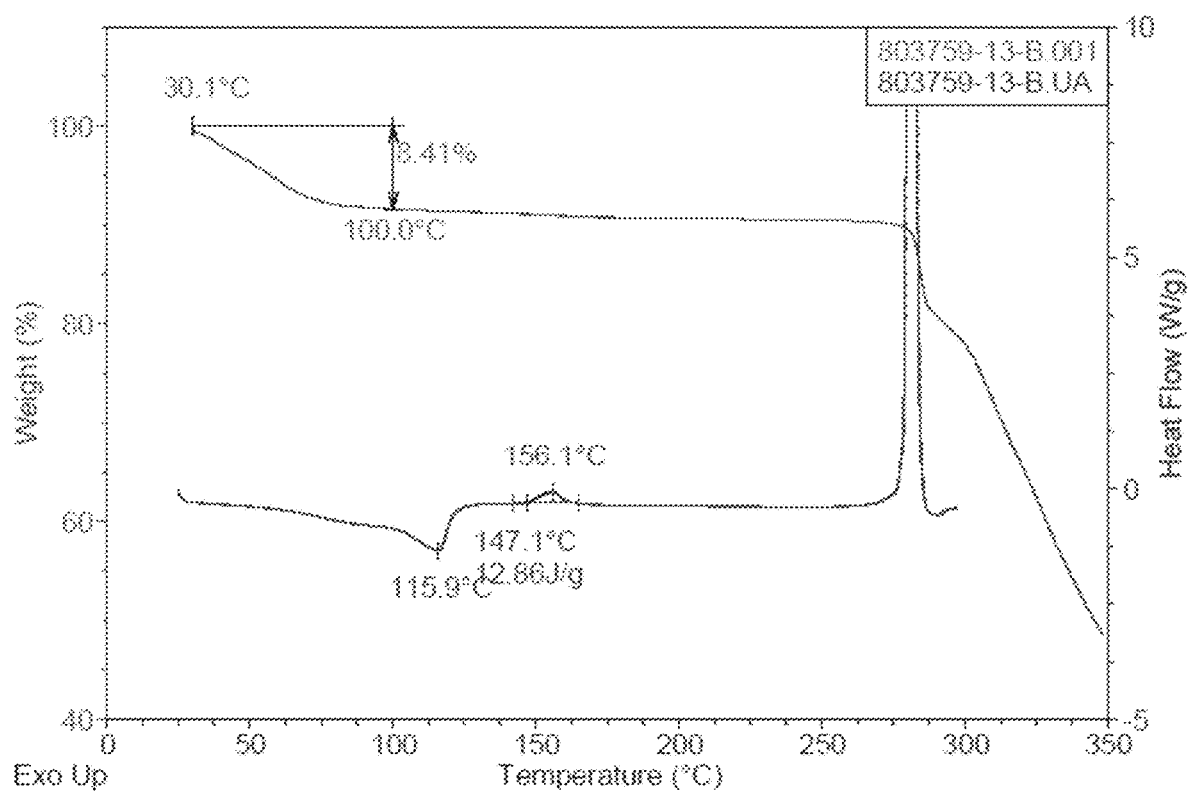
FIG. 9B shows a DSC curve and TGA curve of Form IV.

In one embodiment, Form IV is characterized by having a DSC thermogram substantially as shown in FIG. 9B.

In one embodiment, Form IV is a trihydrate which is isolated from solvents with high water activity. The crystal morphology is needles. The trihydrate dehydrates thermally with the half-point of dehydration at about 60° C.

In yet another embodiment, the invention provides a nanosuspension of tegavivint wherein the nanosuspension was prepared by a process comprising using Form IV as the starting material and milling Form IV at a temperature of between about 40° C. and about 60° C., most preferably at about 60° C.

In one embodiment, if the milling process is done a temperature of less than about 60° C., the nanosuspension has to further undergo the annealing process at or above 60° C.

In another embodiment of the invention, pharmaceutical compositions are provided for use in the methods comprising stable nanosuspensions of Form I prepared using Form IV as the starting material, and pharmaceutically acceptable excipient.

In another embodiment of the invention, provided herein are methods for preventing, treating or ameliorating cancer or tumor metastasis in a mammal in need thereof comprising administering to said mammal an effective amount of the compositions of the invention.

The crystalline forms of tegavivint may be formulated by any method well known in the art and may be prepared for administration by any route, including, without limitation, parenteral, oral, sublingual, transdermal, topical, intranasal, intratracheal, or intrarectal. In certain embodiments, the crystalline form of tegavivint is administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The pharmaceutical compositions comprising a crystalline form of tegavivint may be used in the methods of use described herein.

The active compound is included in the pharmaceutically acceptable carrier or diluent in an amount sufficient to deliver to a patient a therapeutically effective amount without causing serious toxic effects in the patient treated. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

In some embodiments of any of the methods described herein, before treatment with the compositions or methods of the invention, the patient may be treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "tegavivint" refers to (9E,10E)-2,7-bis((3,5-dimethylpiperidin-1-yl)sulfonyl)anthracene-9,10-dione dioxime.

As used herein, the term "Form IV" or "Crystalline Form IV" when used alone refers to Crystalline Form IV of (9E,10E)-2,7-bis((3,5-dimethylpiperidin-1-yl)sulfonyl)anthracene-9,10-dione dioxime.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject is suspected of having a multi-tyrosine kinase-associated cancer.

As used herein, a "therapeutically effective amount" of a crystalline form of tegavivint is an amount that is sufficient to ameliorate, or in some manner reduce a symptom or stop or reverse progression of a condition, or negatively modulate or inhibit the activity of a multi-tyrosine kinase. Such amount may be administered as a single dosage or may be administered according to a regimen, whereby it is effective.

As used herein, "treatment" means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of a crystalline form of tegavivint detailed herein or a pharmaceutically acceptable salt thereof, or the length of treatment time described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg.

Likewise, about 5% or more, 10% or more, 15% or more, 20% or more, and 25% or more means about 5% or more, about 10% or more, about 15% or more, about 20% or more, and about 25% or more.

As used herein, the term "about" when used in reference to XRPD peak positions refers to the inherent variability of peaks depending on the calibration of the instrument, processes used to prepare the crystalline forms of the present invention, age of the crystalline forms and the type of instrument used in the analysis. The variability of the instrumentation used for XRPD analysis was about ±0.2°2θ.

As used herein, the term "about" when used in reference to DSC endothermic peak onset refers to the inherent variability of peaks depending on the calibration of the instrument, method used to prepare the samples of the present invention, and the type of instrument used in the analysis. The variability of the instrumentation used for DSC analysis was about ±2° C.

General Methods

The general methods outlined below were used in the exemplified Examples, unless otherwise noted.

Crystalline forms of the present invention may be prepared using a variety of methods well known to those skilled in the art including crystallization or recrystallization from a suitable solvent or by sublimation. A wide variety of techniques may be employed, including those in the exemplified Examples, for crystallization or recrystallization including evaporation of a water-miscible or a water-immiscible solvent, crystal seeding in a supersaturated solvent mixture, decreasing the temperature of the solvent mixture, or freeze drying the solvent mixture.

In the present invention, crystallization may be done with or without crystal seed. The crystal seed may come from any previous batch of the desired crystalline form. The addition of crystal seed may not affect the preparation of the crystalline forms in the present invention.

The sample was recovered after completion of the isotherm and re-analyzed by XRPD.

Abbreviations and Acronyms

| Category | Abbreviations | Full Name/Description |
|---|---|---|
| Analytical Techniques | DSC | Differential Scanning Calorimetry |
| | DVS | Dynamic Vapor Sorption |
| | NMR | Nuclear Magnetic Resonance |
| | PLM | Polarized light microscopy |
| | PSD | Particle Size Distribution |
| | TGA | Thermogravimetric Analysis |
| | XRPD | X-ray Powder Diffraction |
| | VT-XRPD | Variable Temperature X-ray Powder Diffraction |
| | ACN | Acetonitrile |
| | $CHCl_3$ | Chloroform |
| | DMF | Dimethylforamide |
| | DMSO | Dimethylsulfoxide |
| | EtOAc | Ethyl acetate |
| | EtOH | Ethanol |
| | IPA | Isopropyl alcohol |
| Solvent | MEK | Methyl ethyl ketone |
| | MeOH | Methanol |
| | MTBE | Methyl-tert-butyl ether |
| | THF | Tetrahydrofuran |
| Other | RT | Room temperature |
| | v/v | percent volume ratio |

The following Examples are intended to illustrate further certain embodiments of the invention and are not intended to limit the scope of the invention.

Example 1

Investigation of Form I of Tegavivint

This Example illustrates the investigation of Form I of tegavivint.

Figure 1:
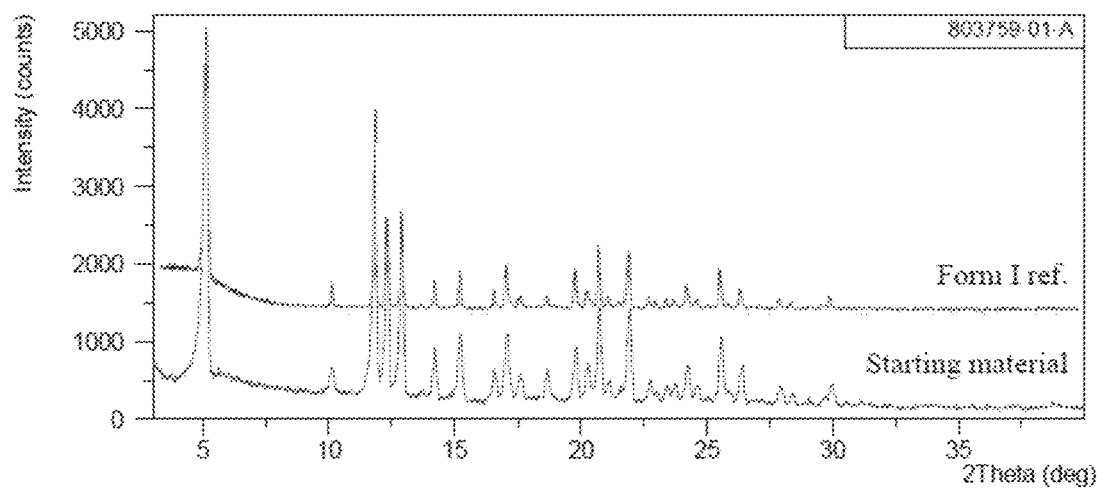
FIG. 1 illustrates an X-ray powder diffraction (XRPD) pattern of Form I of tegavivint.
Figure 2:
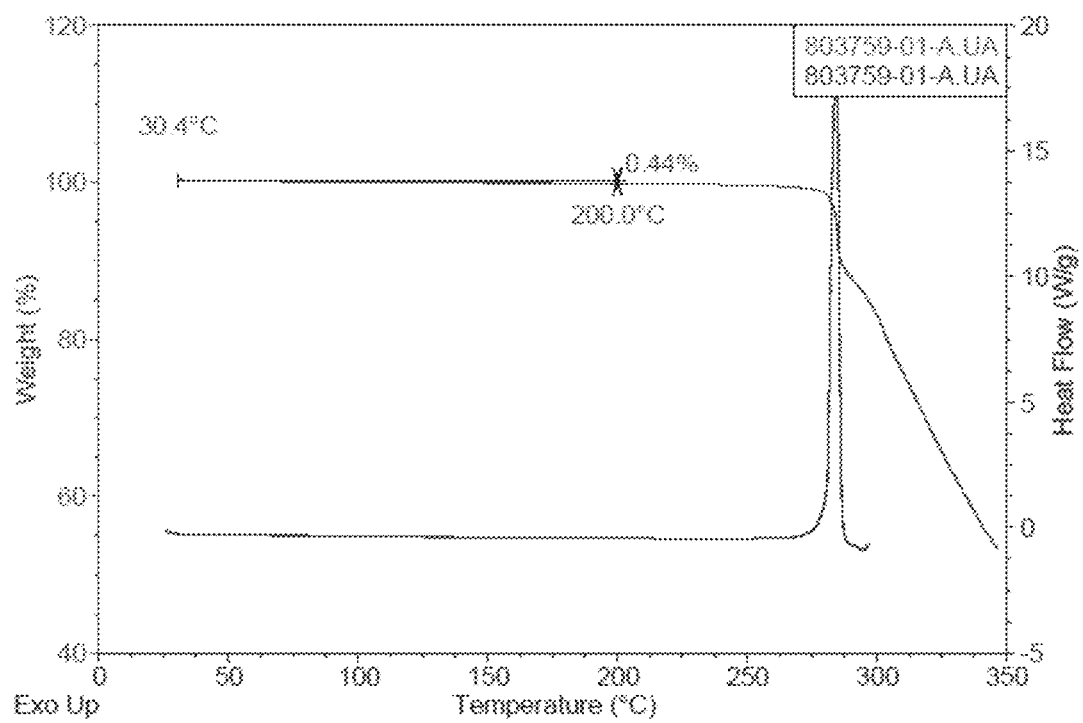
FIG. 2 illustrates a differential scanning calorimetry (DSC) curve and Thermogravimetric Analysis (TGA) curve of Form I.
Figure 3:
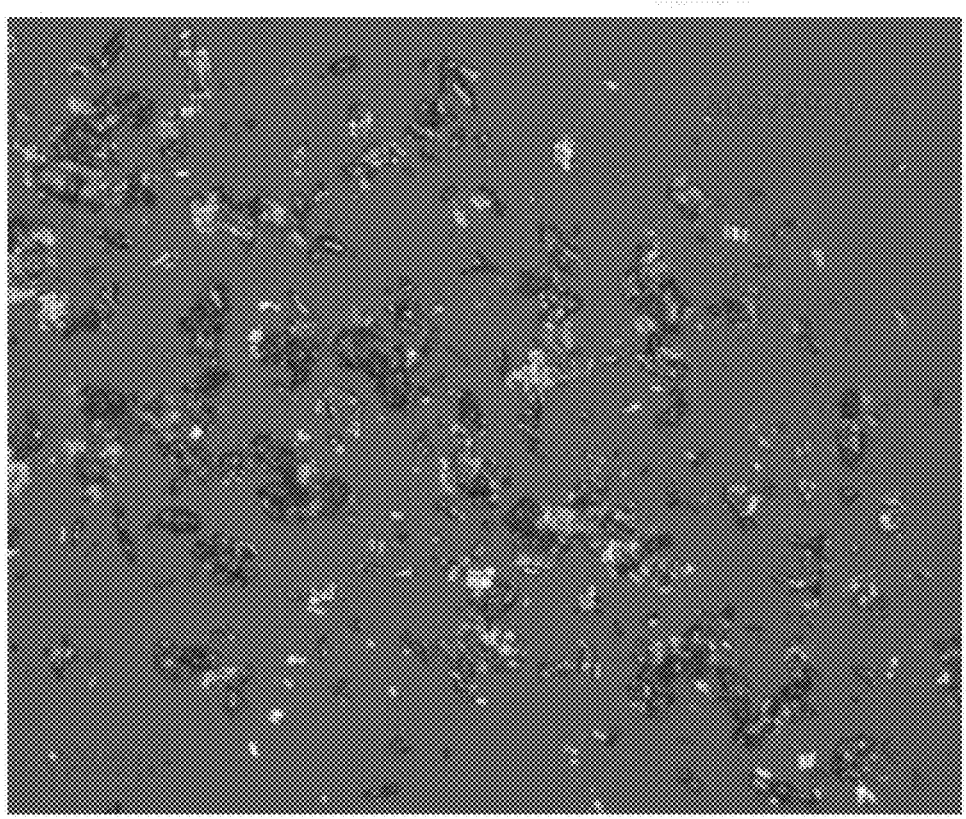
FIG. 3 shows a Polarized Light Microscopy (PLM) image of Form I.

Starting material (Form I of tegavivint) was characterized by XRPD, TGA, DSC and PLM. XRPD pattern displayed in FIG. 1 showed the starting material was crystalline and confirmed to be Form I. TGA and DSC curves are displayed in FIG. 2. A weight loss of 0.4% up to 150° C. was observed on TGA curve, and DSC result showed no melting endotherm before decomposition. Based on the characterization results, Form I was speculated to be an anhydrate. PLM image displayed in FIG. 3 showed irregular fine particles with partial aggregation for Form I sample.

Example 2

Preparation of Form II of Tegavivint

Figure 4:
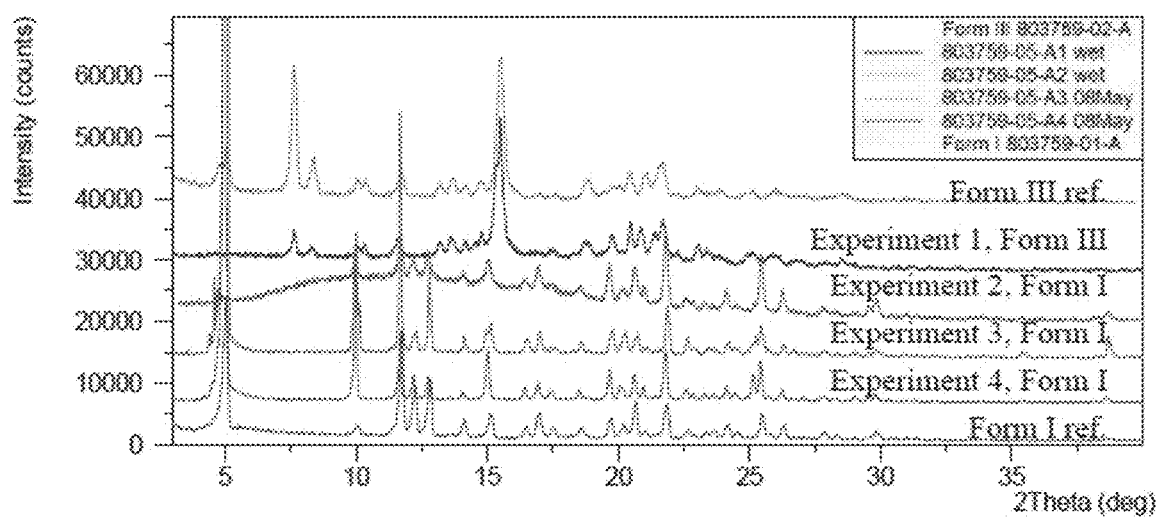
FIG. 4 shows XRPD patterns overlay of Form II preparation.

Attempts to prepare Form II of tegavivint were performed in four conditions. The detailed results are shown in FIG. 4 and Table 1. The results suggested that Form II was quite challenging to be re-prepared or metastable.

TABLE 1

Summary of Form II Preparation Attempts

| ID | Method | Solvent, mL | Anti-solvent, mL | Results |
|---|---|---|---|---|
| 803759-05-A1 | Anti-solvent addition | EtOH, 2.5 | $H_2O$, 2 | Form III |

TABLE 1-continued

Summary of Form II Preparation Attempts

| ID | Method | Solvent, mL | Anti-solvent, mL | Results |
|---|---|---|---|---|
| 803759-05-A2 | Anti-solvent addition | EtOH, 2.5 | $H_2O$, 2 | Form I |
| 803759-05-A3 | Solution vapor diffusion | EtOH, 2 | $H_2O$ | Form I |
| 803759-05-A4 | Slow evaporation | EtOH, 2 | n-heptane, 2 | Form I |

Example 3

Preparation of Form III of Tegavivint

Figure 5:
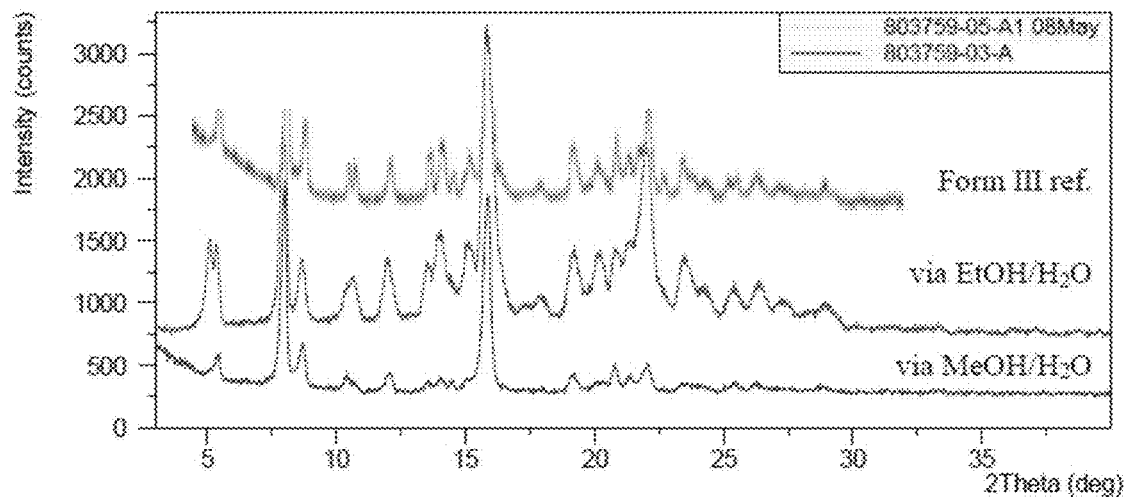
FIG. 5 shows XRPD patterns overlay of Form III preparation.
Figure 6:
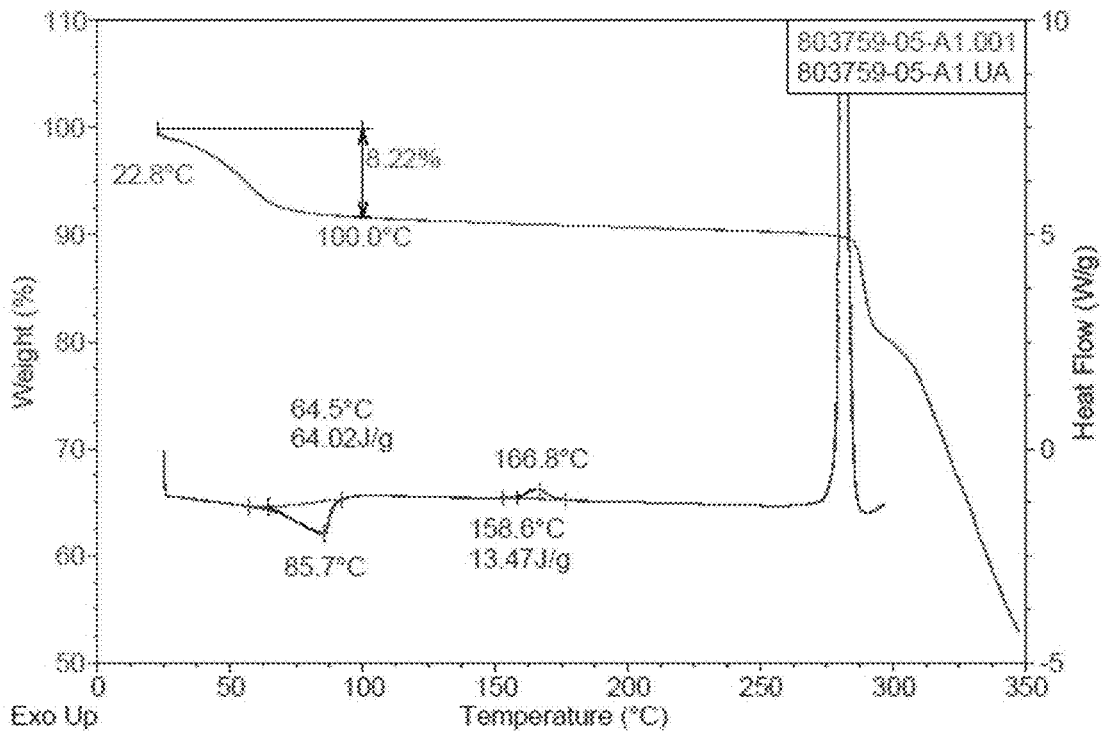
FIG. 6 illustrates a DSC curve and TGA curve of Form III.
Figure 7:
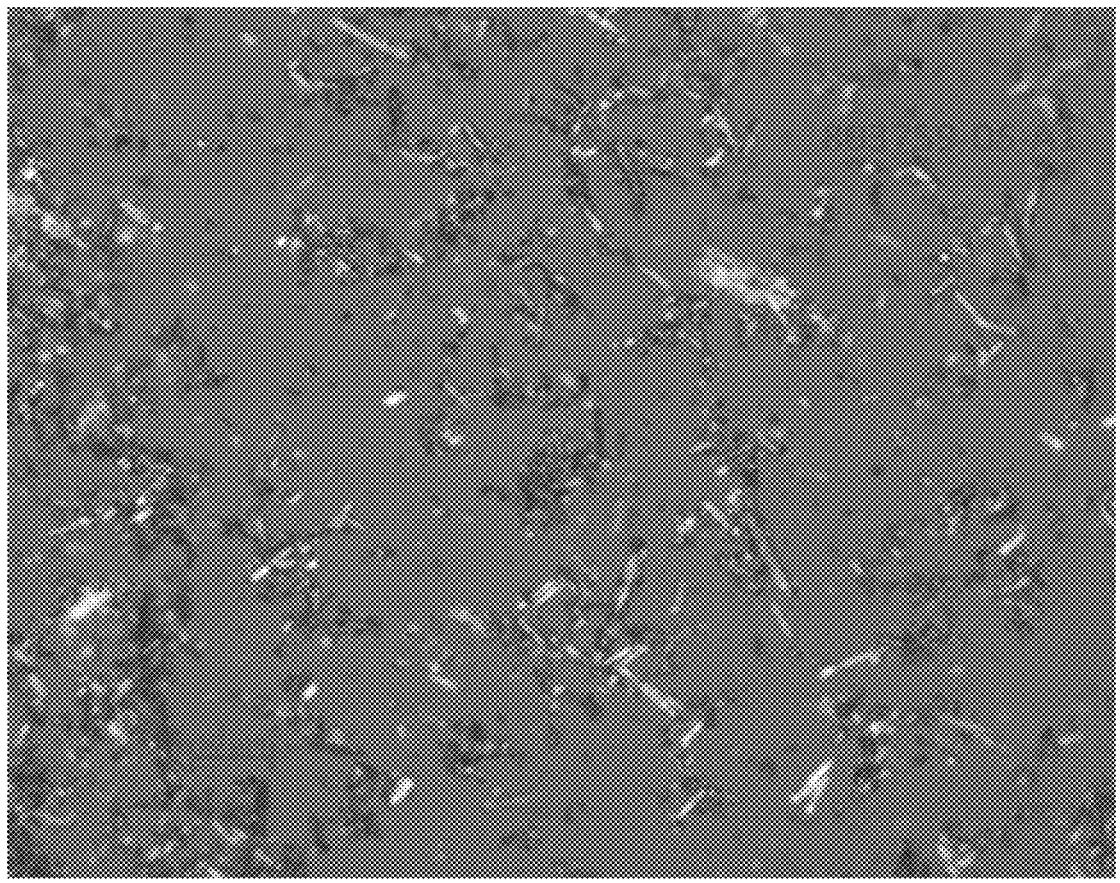
FIG. 7 shows a PLM image of Form III.

Form III samples (803759-03-A and 803759-05-A1) were prepared via anti-solvent addition in MeOH/$H_2O$ and EtOH/$H_2O$ systems, and the XRPD results are displayed in FIG. 5. The TGA/DSC results of Form III (803759-05-A1) are displayed in FIG. 6. A weight loss of 8.2% up to 100° C. was observed on TGA. One endotherm at 64.5° C. and one exotherm at 158.6° C. were observed before decomposition on DSC. The PLM image displayed in FIG. 7 showed needle-like and fine particles with aggregation for Form III sample (803759-05-A1).

Figure 8:
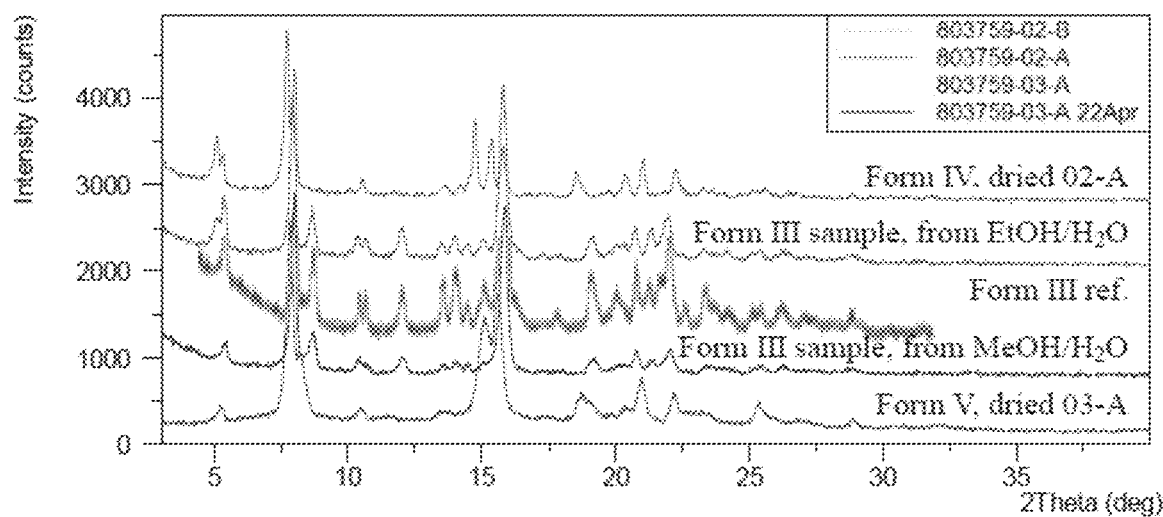
FIG. 8 shows XRPD patterns overlay of Form III samples after drying.

Since Form III samples could be obtained from different solvent systems and converted to Form IV after vacuum drying at RT or Form V after exposure to ambient condition at RT (FIG. 8), Form III might be isomorphic.

Example 4

Preparation of Form IV of Tegavivint

Form IV (803759-13-B) sample was re-prepared at 2-g scale. The detailed procedures were as follows:
1. Weigh 2.0 g 803759-01-A sample into a 1-L reactor.
2. Charge 200 mL EtOH, and stir at RT with 300 rpm to obtain a clear solution
3. Charge 100 mL water.
4. Add 90.2 mg Form IV seed, a suspension was observed.
5. Charge 100 mL water over 1 h.
6. Keep slurry for 2 h.
7. Filter and test XRPD of the wet cake.
8. Transfer the wet cake into a 1-L reactor, charge 200 mL water and slurry overnight.
9. Filter and vacuum dry for 4 hrs. 1.9 g solids were obtained (803759-13-B, Form IV).

Figure 9C:
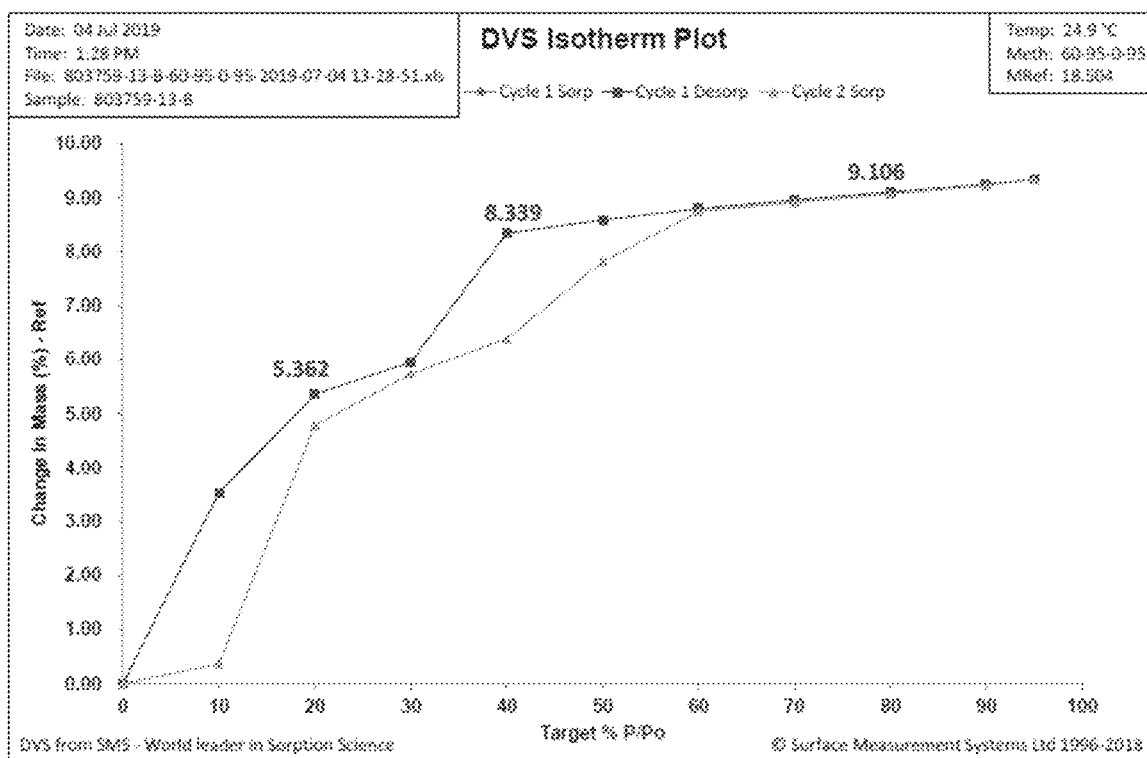
FIG. 9C shows a Dynamic Vapor Sorption (DVS) profile of Form IV.
Figure 9D:
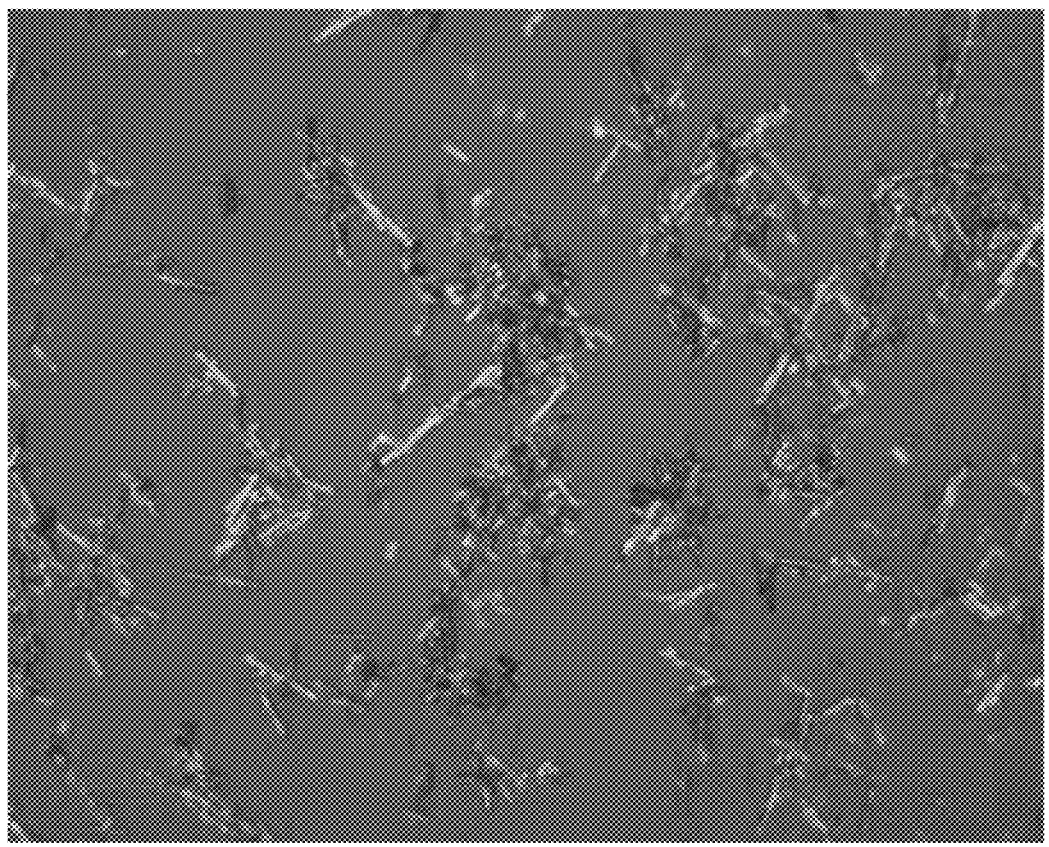
FIG. 9D shows a PLM image of Form IV.

The XRPD results of Form IV are displayed in FIG. 9A. The TGA/DSC results were displayed in FIG. 9B. A weight loss of 8.4% up to 150° C. could be observed on TGA. One endotherm at 115.9° C. (peak) and one exotherm at 147.1° C. (onset) before decomposition were observed on DSC. DVS result displayed in FIG. 9C showed that: 1) two platforms were observed indicating two potential hydrate forms existing. 2) A water uptake of 9.1% was observed at 25° C./80% RH, which was consistent with TGA weight loss of Form IV. The PLM image displayed in FIG. 9D showed needle-like particles was observed for Form IV sample (803759-13-B).

Figure 9E:
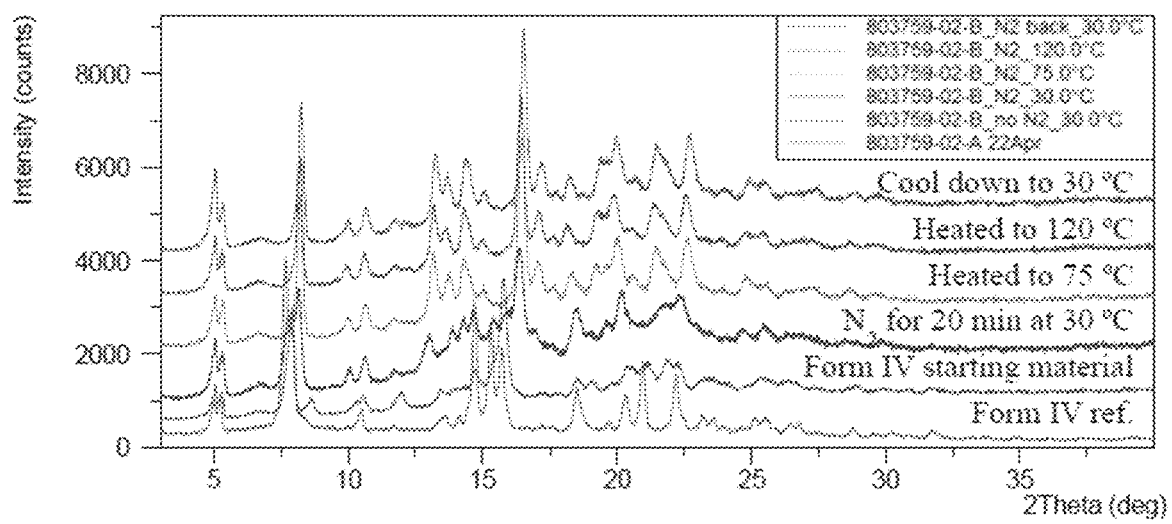
FIG. 9E shows Variable Temperature X-ray Powder Diffraction (VT-XRPD) profile of Form IV.
Figure 9F:
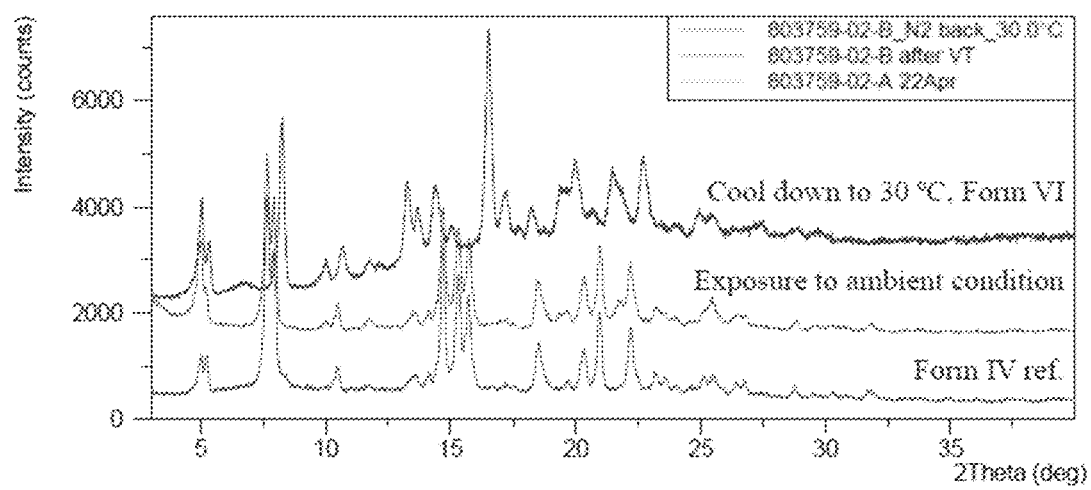
FIG. 9F shows XRPD patterns overlay of Form IV sample after VT-XRPD and exposure to ambient conditions.

VT-XRPD test was employed for further investigation of Form IV, the results displayed in FIG. 9E and FIG. 9F showed that 1) Form IV sample partially converted to a new form at 30° C. under $N_2$, and the new form was named as Form VI. 2) After heating to 75 and 120° C., pure Form VI was observed. 3) After cooling to 30° C., Form VI was still observed. 4) After exposure to ambient condition, Form VI converted to Form IV quickly. Thus, Form IV is believed to be a hydrate.

Example 5

Preparation of Form V of Tegavivint

Figure 10:
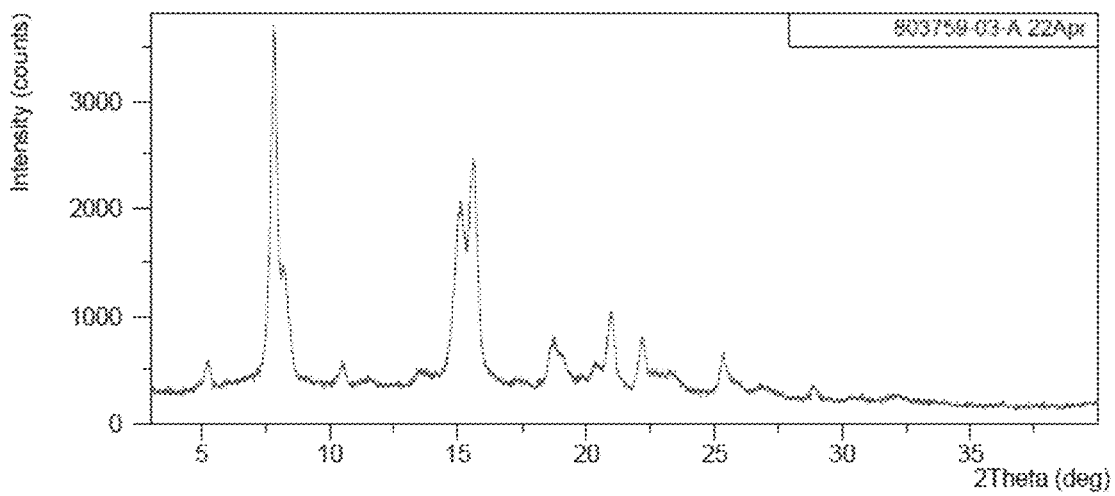
FIG. 10 shows XRPD pattern of Form V.

Form V sample (803759-03-A 22Apr) was obtained via drying Form III sample (803759-03-A) at ambient condition, the XRPD pattern was displayed in FIG. 10. The TGA and DSC data were not collected due to limited solid.

Example 6

Preparation of Form VI of Tegavivint

Figure 11:
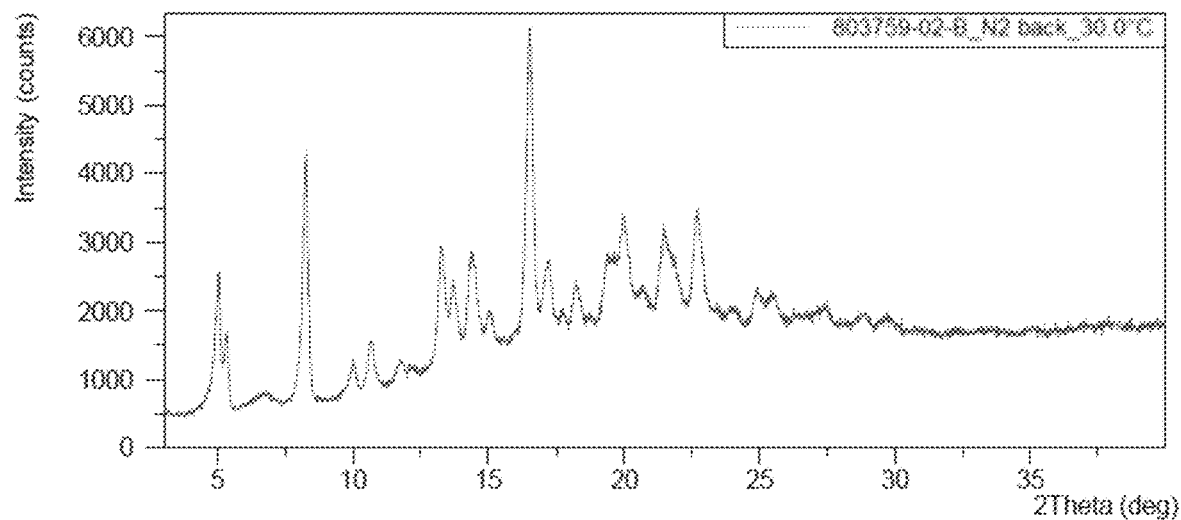
FIG. 11 shows XRPD pattern of Form VI.

Form VI sample (803759-02-B_N2 back_30.0° C.) was obtained during VT-XRPD test for Form IV sample (803759-02-B). The XRPD pattern is displayed in FIG. 11. After exposure to ambient condition, Form VI converted to Form IV quickly (FIG. 9F). Since Form VI was unstable under ambient condition, no further characterization data was collected for Form VI, and Form VI was speculated to be anhydrate.

Example 7

Preparation of Amorphous Form of Tegavivint

Figure 12A:
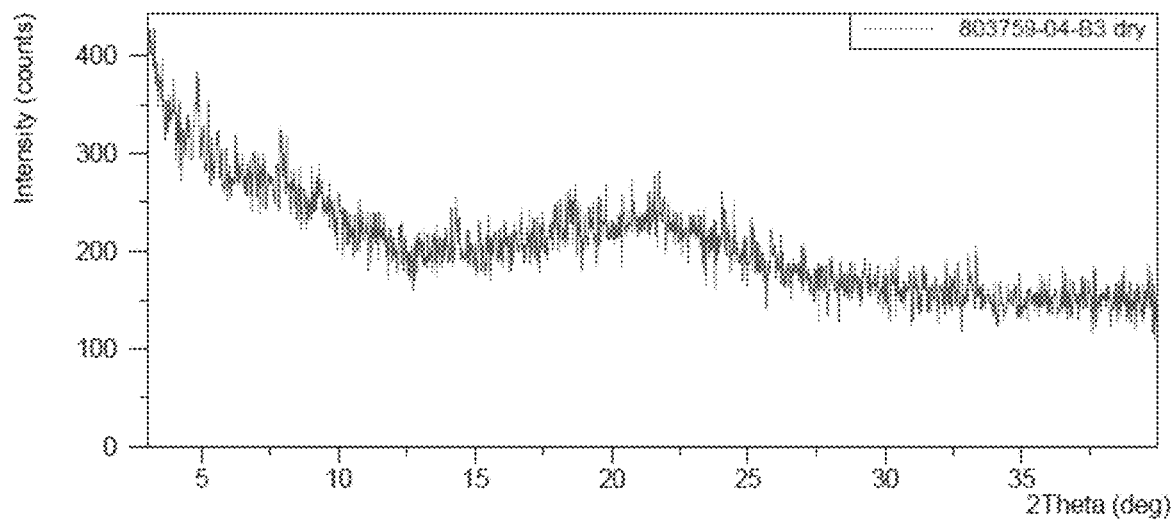
FIG. 12A illustrates XRPD pattern of amorphous sample.
Figure 12B:
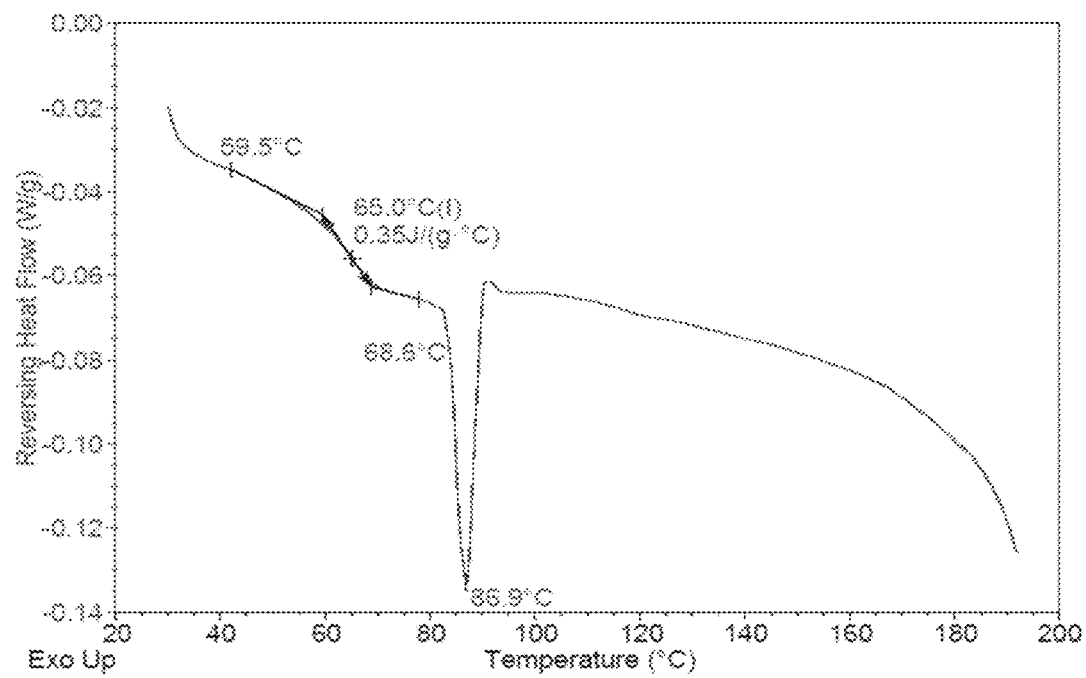
FIG. 12B shows a modulate DSC (mDSC) curve of amorphous sample.

Amorphous sample (803759-04-B3 dry) was prepared by reverse anti-solvent addition in DMSO/$H_2O$ system and vacuum drying at RT. The XRPD pattern is displayed in FIG. 12A. The mDSC result displayed in FIG. 12B showed the Tg of the amorphous sample was 65.0° C. (middle temperature).

Example 8

Slurry Competition Experiments

To determine the most stable form under high water activity at RT, slurry competition of Form I, III, IV and V was performed in three solvent systems (water, ACN/$H_2O$ (1:1, v/v) and ACN/$H_2O$ (1:3, v/v)) with high water activity at RT.

The detailed procedure was as follows:
1) Prepare saturated solution with Form I sample (803759-01-A) in three solvent systems.
2) Add about 10 mg of each form into 1 mL corresponding saturated solution.
3) Slurry and check the XRPD of the wet cake after one day and six days.

Figure 13A:
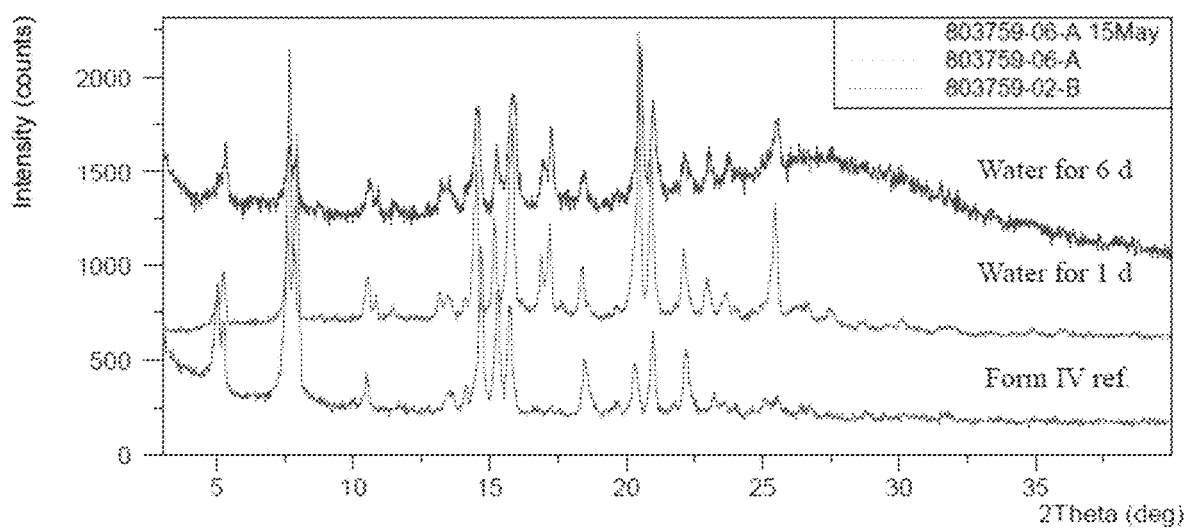
FIG. 13A shows XRPD pattern of solid obtained from slurry competition in water.
Figure 13B:
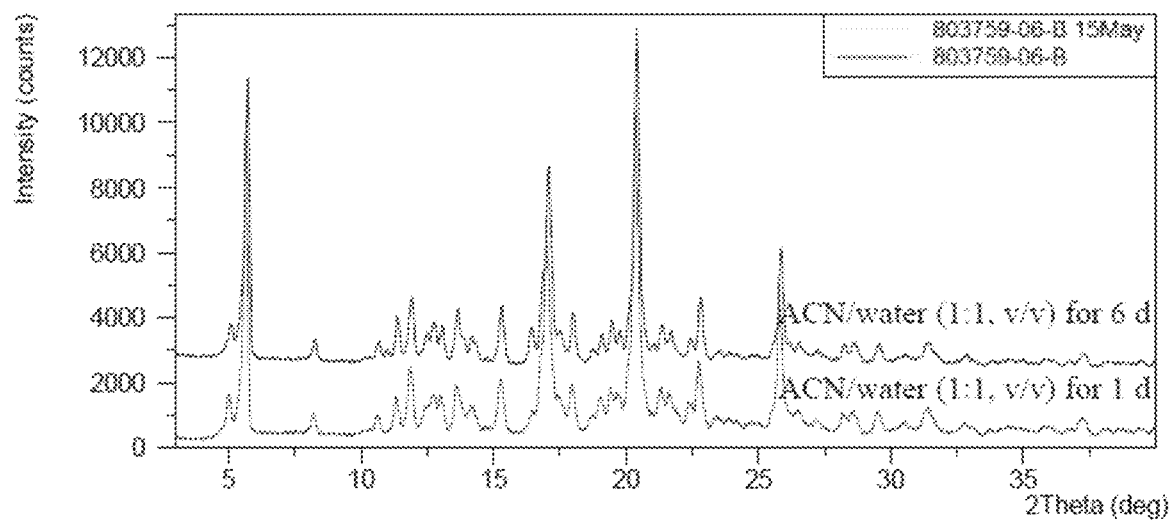
FIG. 13B shows XRPD pattern of solid obtained from slurry competition in ACN/water (1:1, v/v).
Figure 13C:
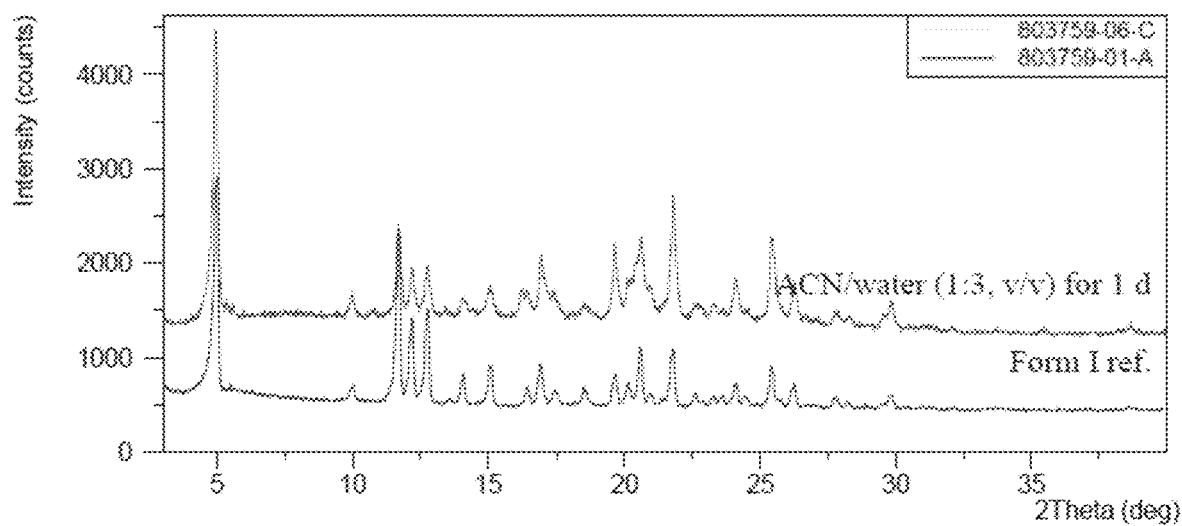
FIG. 13C shows XRPD pattern of solid obtained from slurry competition in ACN/water (1:3, v/v).

The results are displayed in Table 2, FIG. 13A, FIG. 13B and FIG. 13C. The results showed:
1) Form IV was obtained from water system.
2) A new form was obtained from ACN/$H_2O$ (1:1, v/v) system, which was speculated to be ACN solvate.
3) Form I was obtained from ACN/$H_2O$ (1:3, v/v) system.

TABLE 2

Summary of slurry competition

| Starting Material | H₂O | ACN/H₂O (1:1, v/v) | ACN/H₂O (1:3, v/v) |
|---|---|---|---|
| Form I (803759-01-A), Form III (803759-05-A1), Form IV (803759-02-B) and Form V (803759-03-A22Apr) | Form IV | New form (speculated to be ACN solvate) | Form I |

Example 9

Ball Milling Experiments

Previously, Form I was milled to a very small particle size and started converting to Form IV in aqueous suspension with unacceptable particle size growth during storage. Therefore, ball milling of Form I and Form IV was performed to evaluate the form stability and particle size growth. The detailed procedure of ball milling was as follows.

1. Suspend Form I and Form IV sample in 1% Poloxamer 188 water solution (50 mg/mL), separately.
2. Add ~12 mL suspension into a 50-mL tube which contained milling beads (the volume of milling beads is around 30 mL). After 12 mL suspension was added, the liquid surface just covered the beads.
3. Roll the 50-mL tube (containing beads and suspension) at 5° C., RT and 60° C. with 30 rpm.
4. Sample ~0.8 mL suspension at 1, 2, 4, 24 h using 1-mL syringe.
5. Test XRPD, PSD and PLM for the suspension.

Figure 14A:
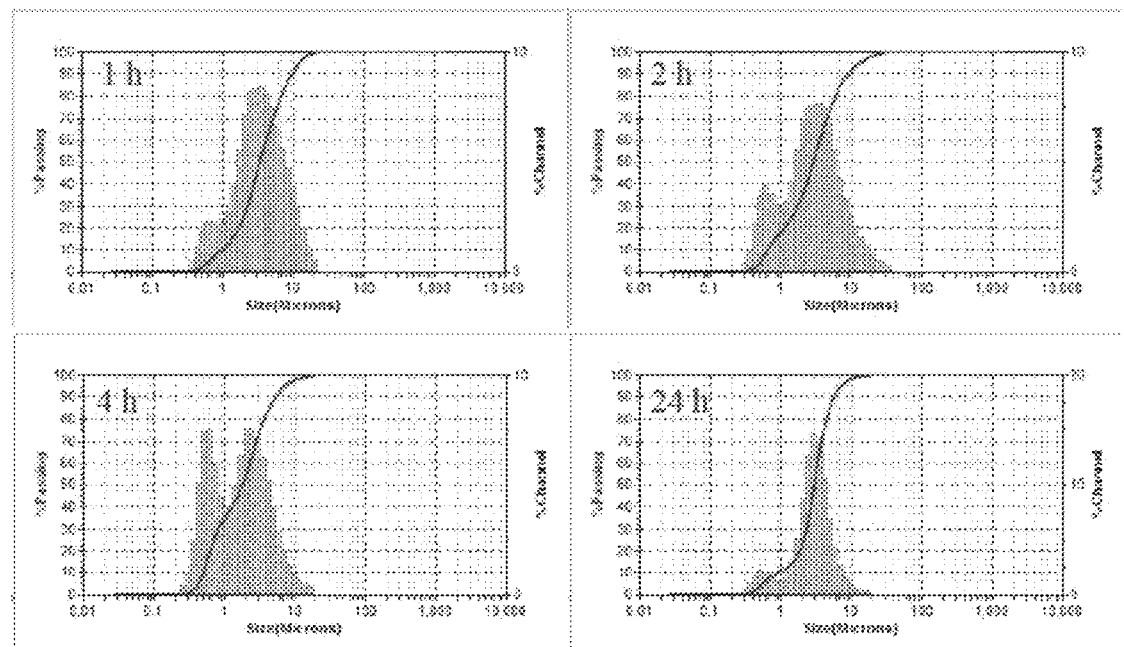
FIG. 14A is a Particle Size Distribution (PSD) plot of Form I sample milled at 5° C.
Figure 14B:
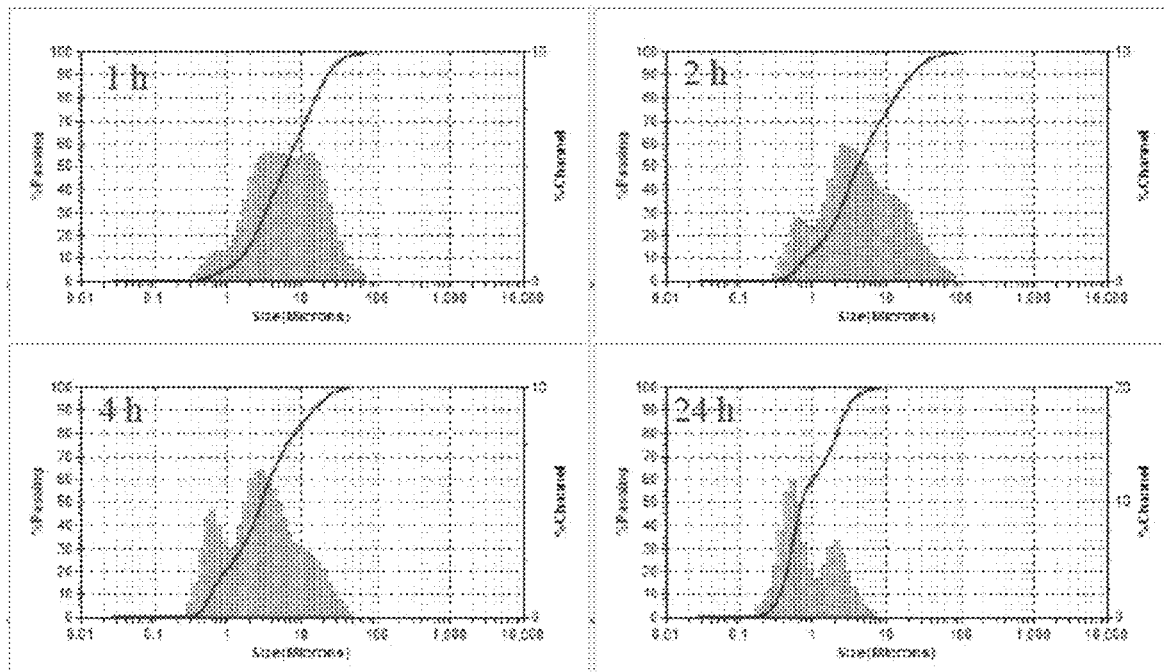
FIG. 14B is a PSD plot of Form I sample milled at RT.
Figure 14C:
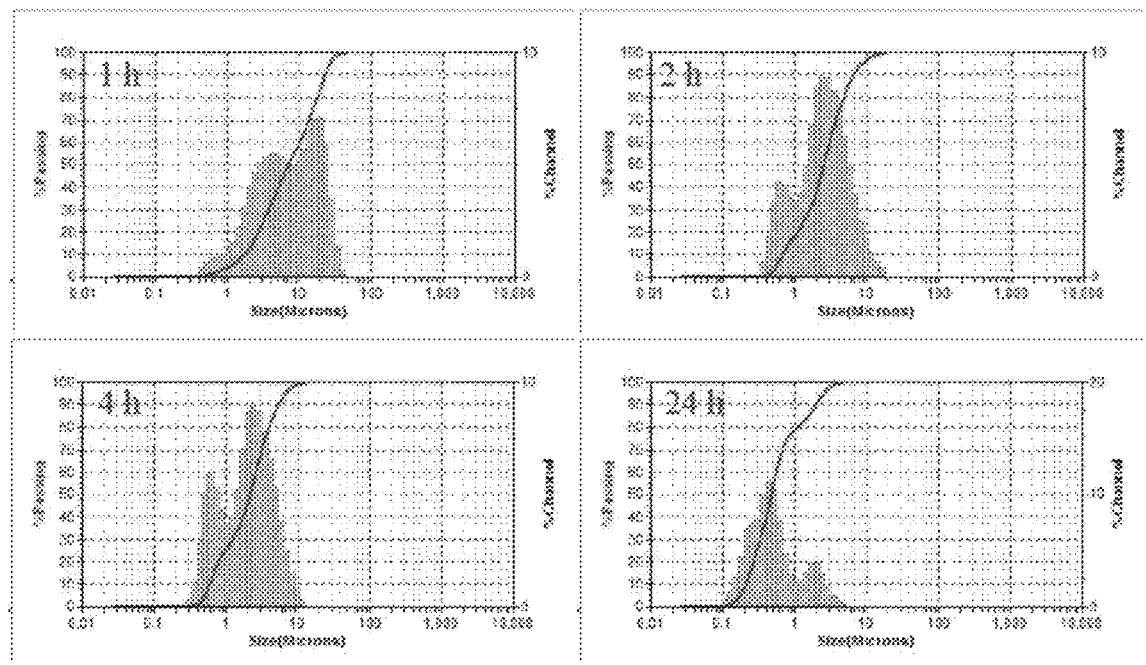
FIG. 14C is a PSD plot of Form I sample milled at 60° C.
Figure 14D:
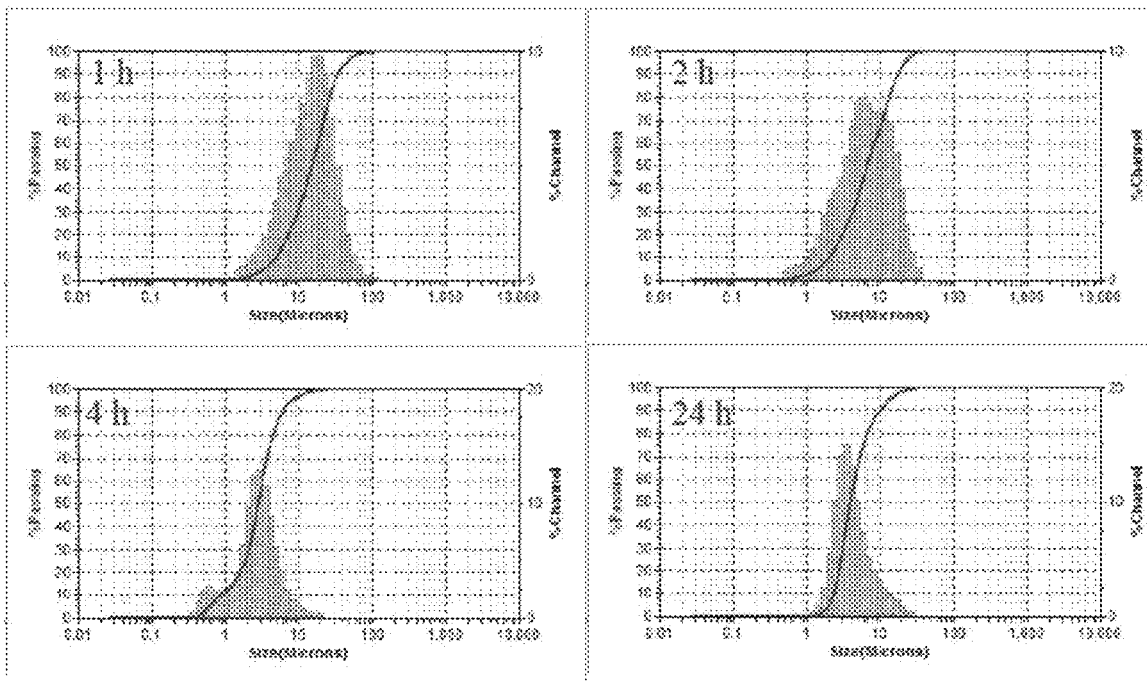
FIG. 14D is a PSD plot of Form IV sample milled at 5° C.
Figure 14E:
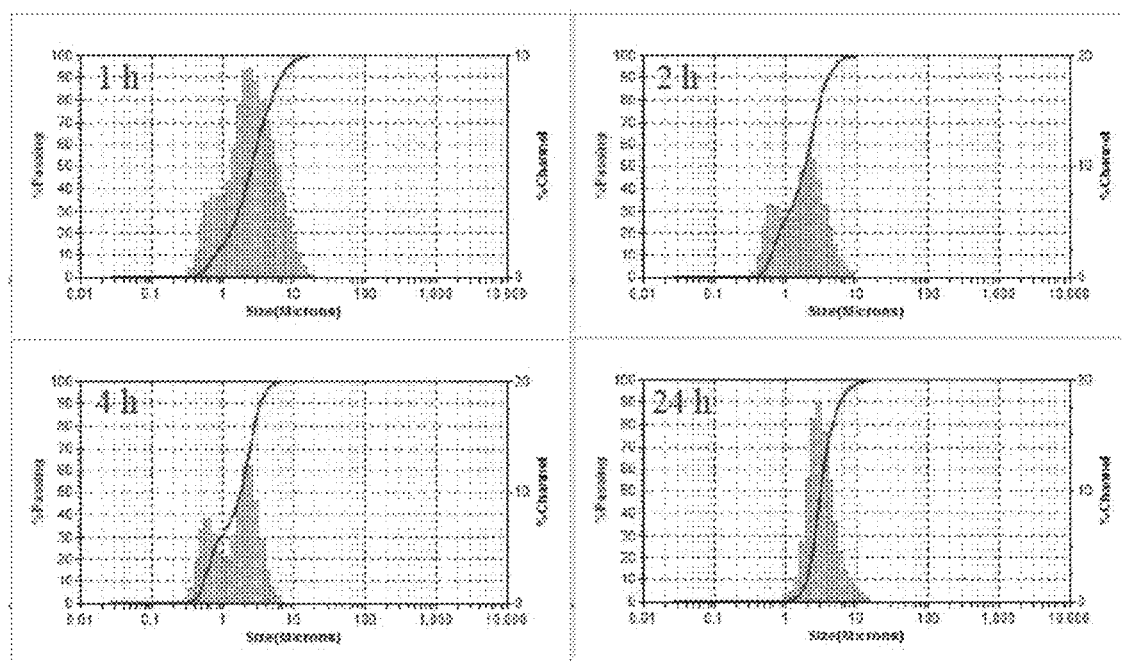
FIG. 14E is a PSD plot of Form IV sample milled at RT.
Figure 14F:
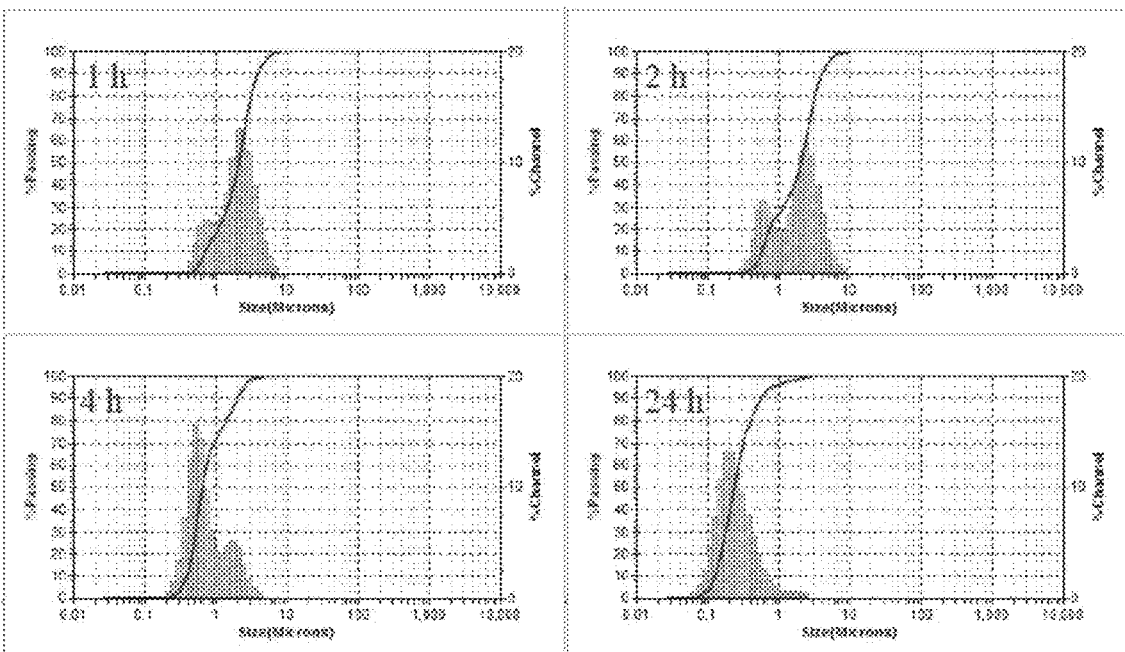
FIG. 14F is a PSD plot of Form IV sample milled at 60° C.
Figure 14G:
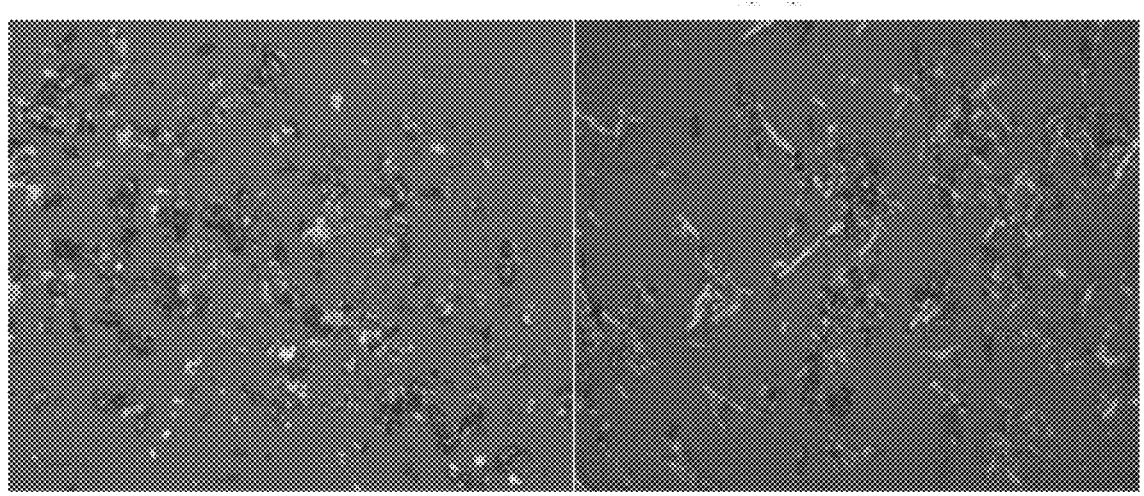
FIG. 14G is a PLM image of Form I and Form IV.
Figure 14H:
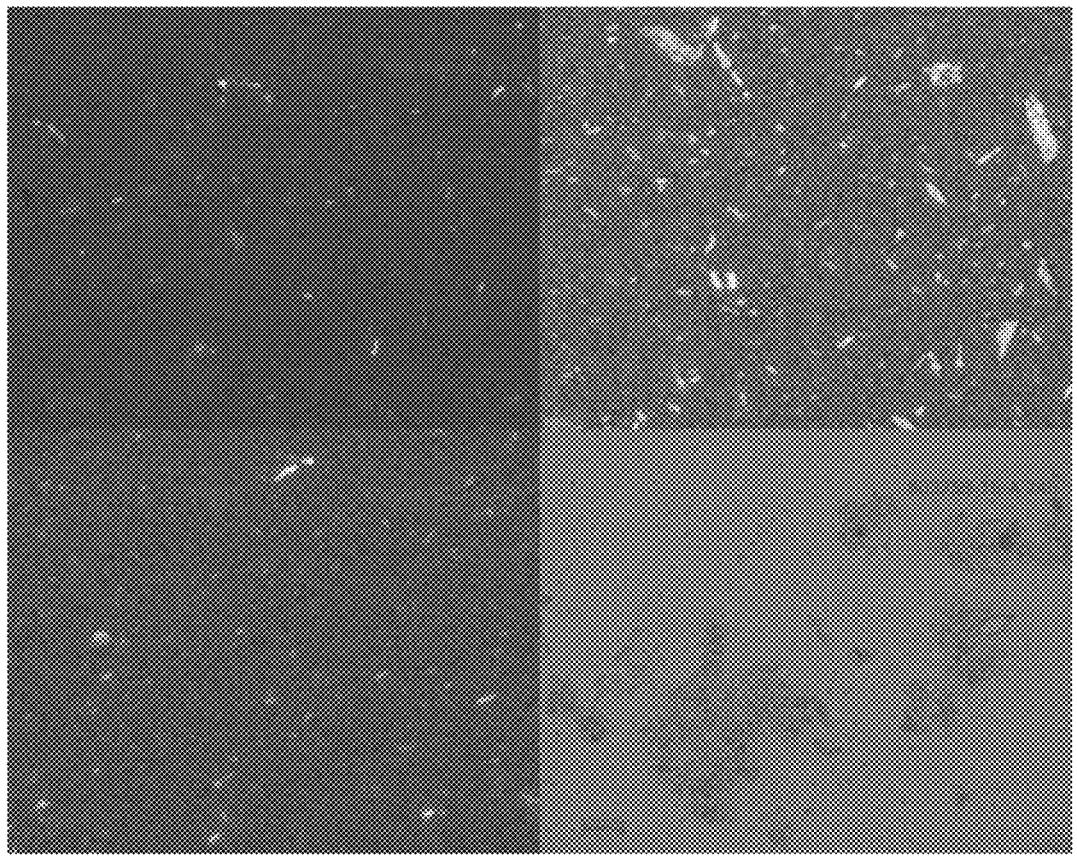
FIG. 14H is a PLM image of Form I sample milled at 5° C.
Figure 14I:
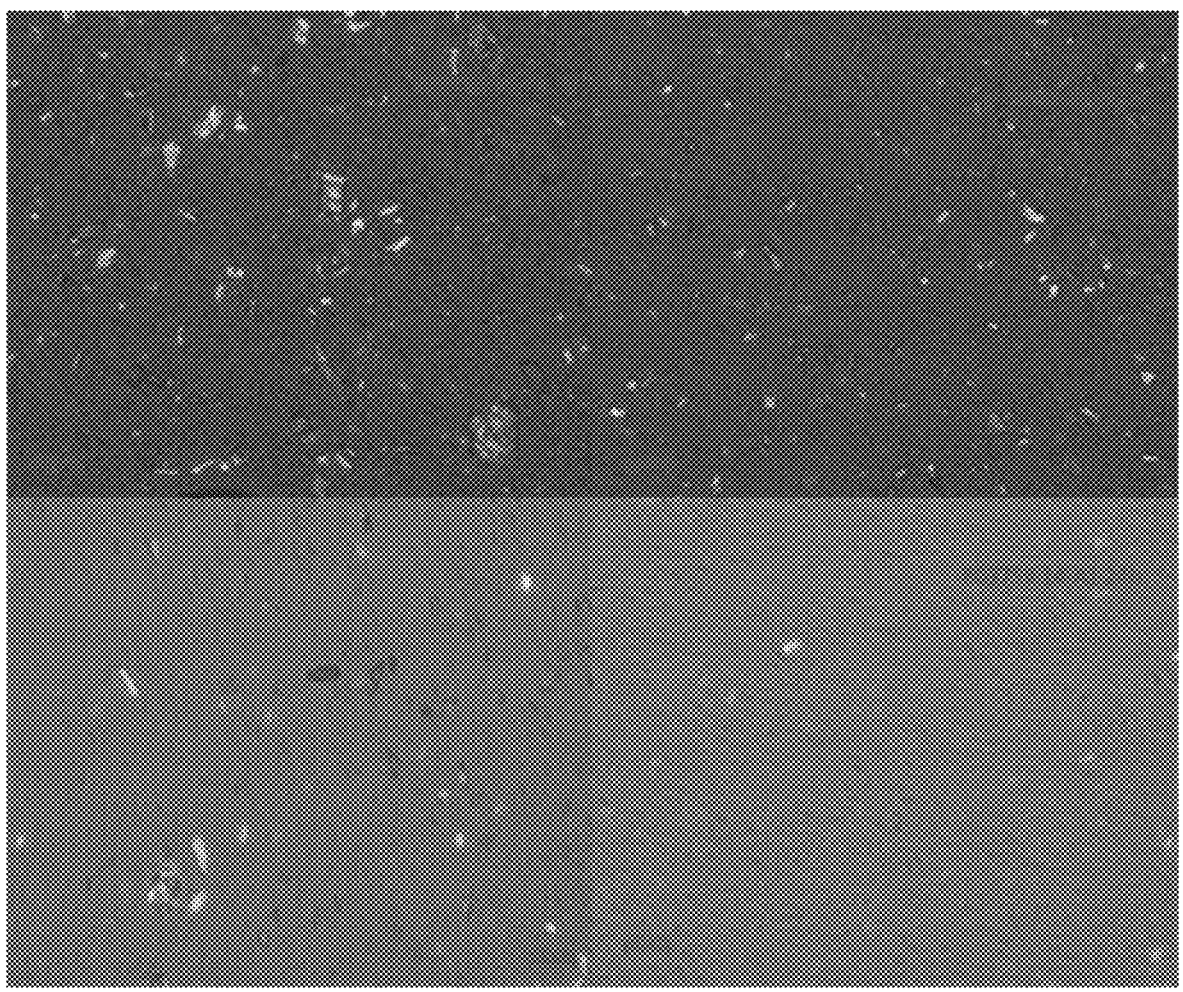
FIG. 14I is a PLM image of Form I sample milled at RT.
Figure 14J:
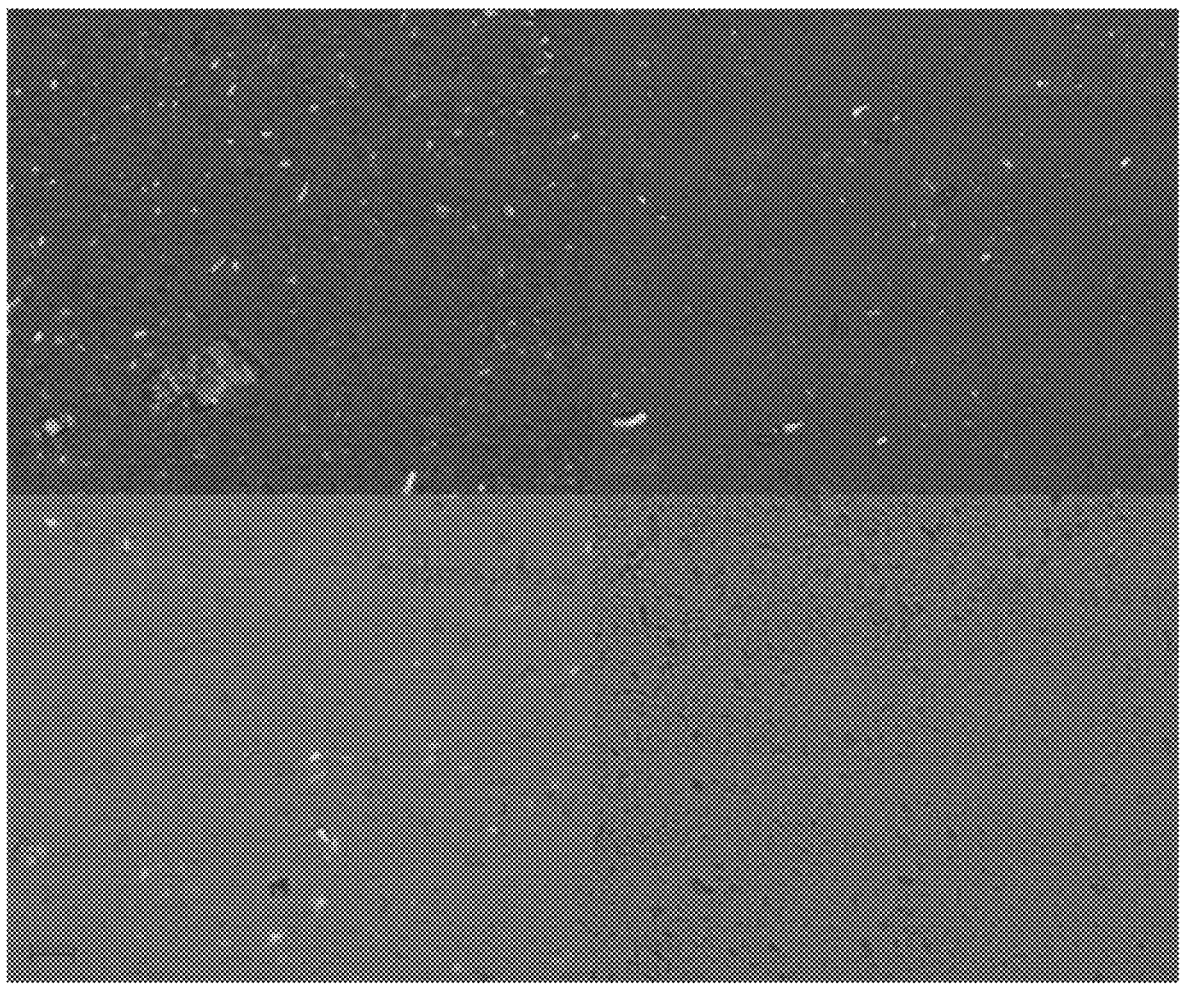
FIG. 14J is a PLM image of Form I sample milled at 60° C.
Figure 14K:
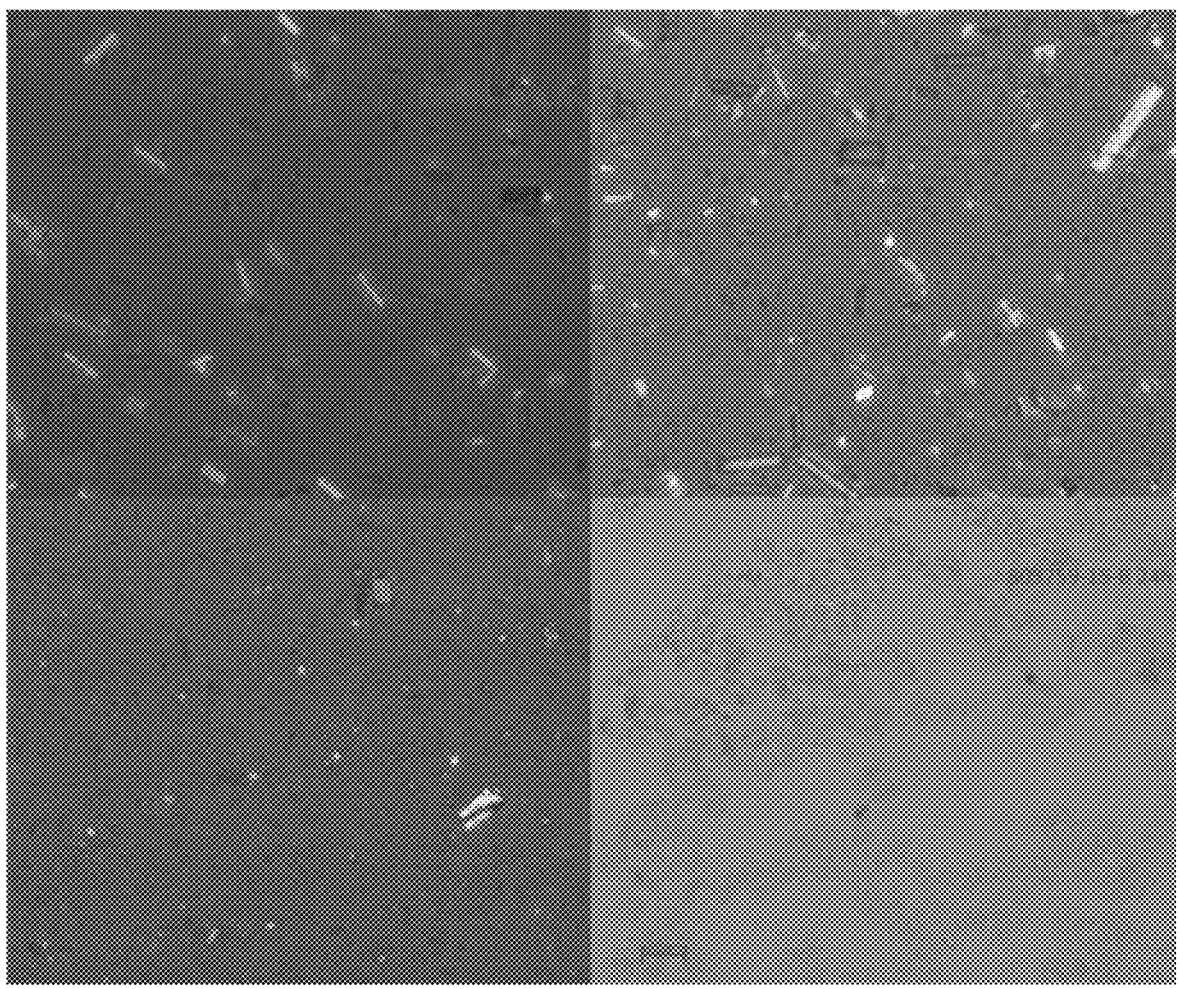
FIG. 14K is a PLM image of Form IV sample milled at 5° C.
Figure 14L:
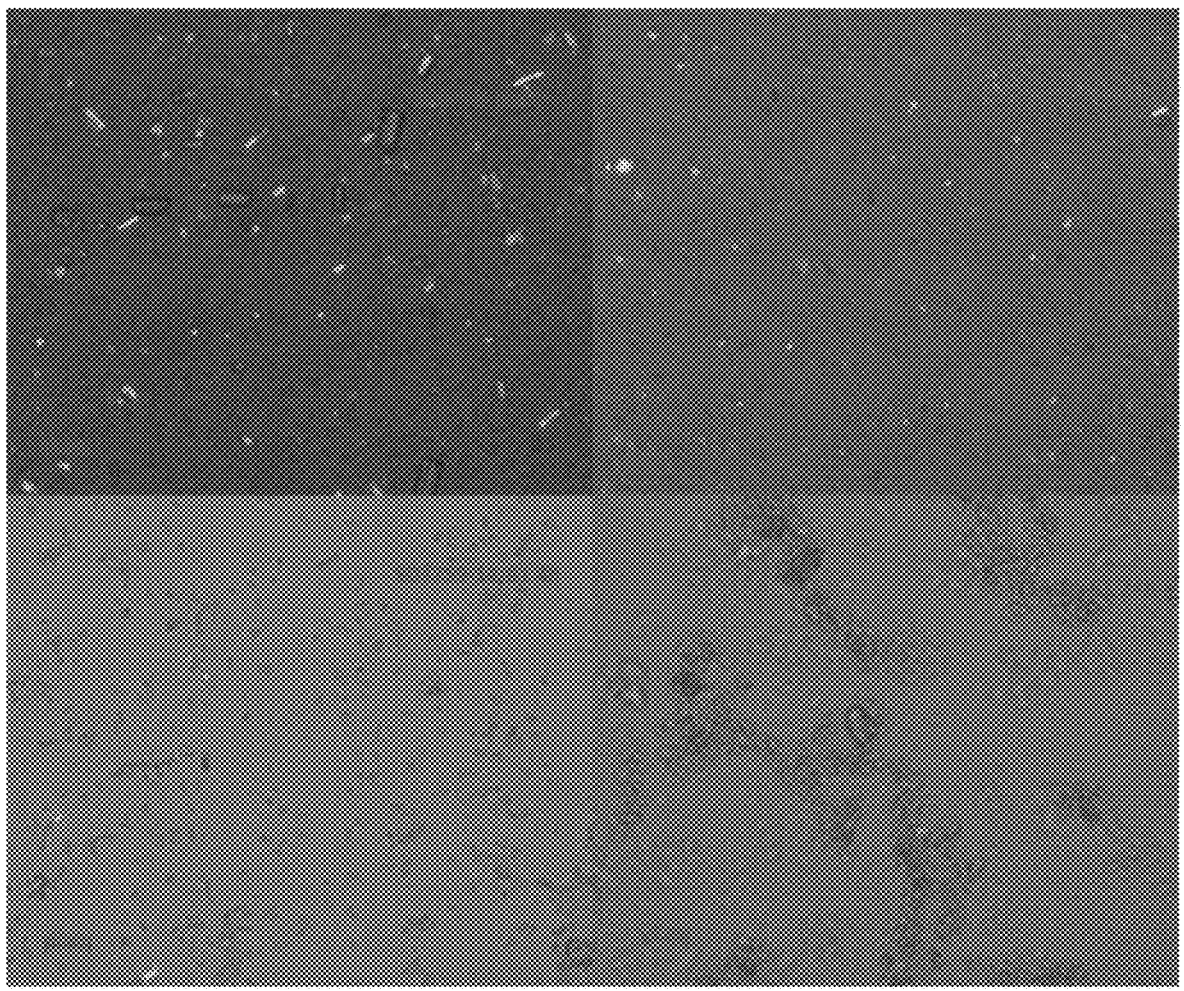
FIG. 14L is a PLM image of Form IV sample milled at RT.
Figure 14M:
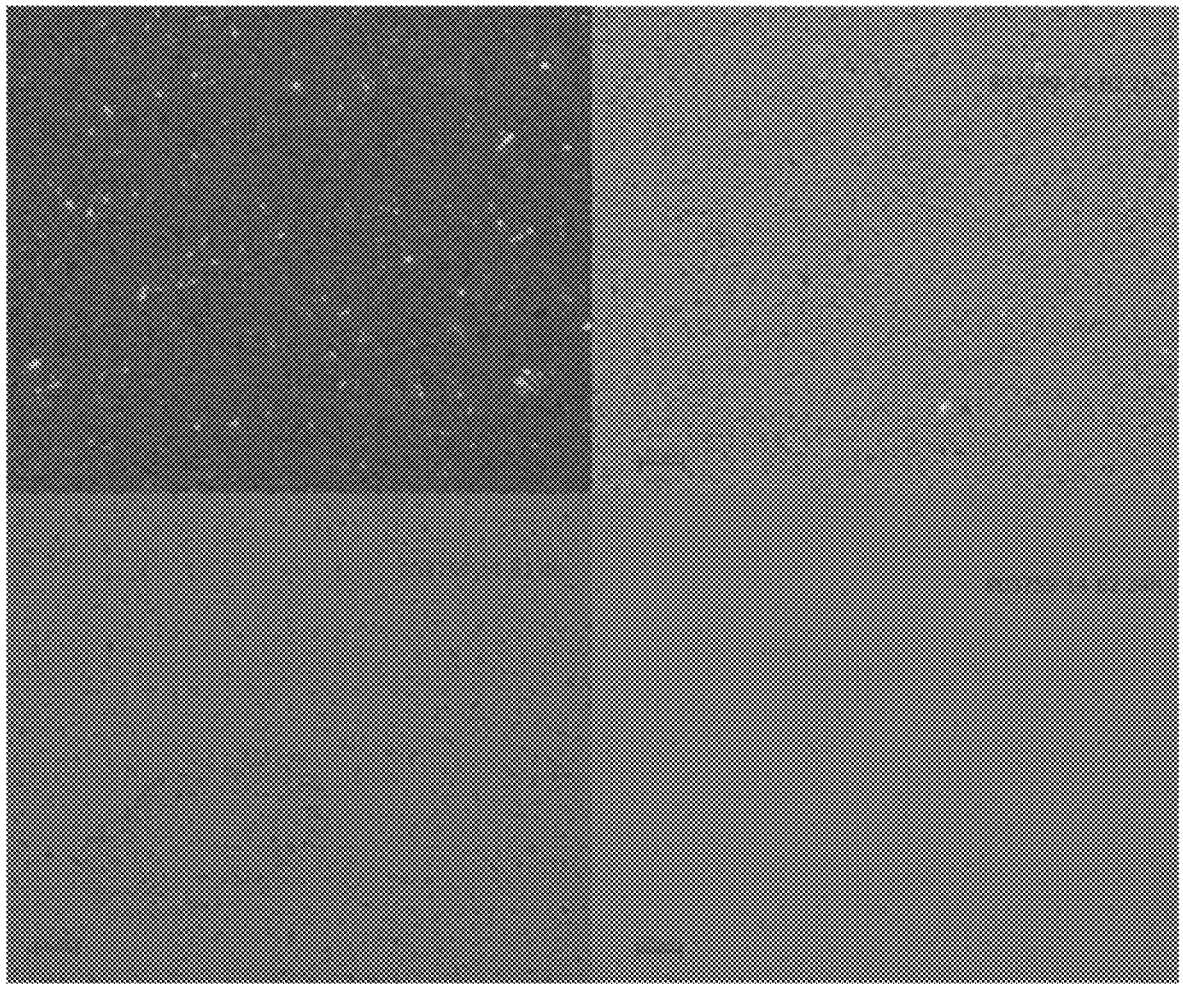
FIG. 14M is a PLM image of Form IV sample milled at 60° C.
Figure 14N:
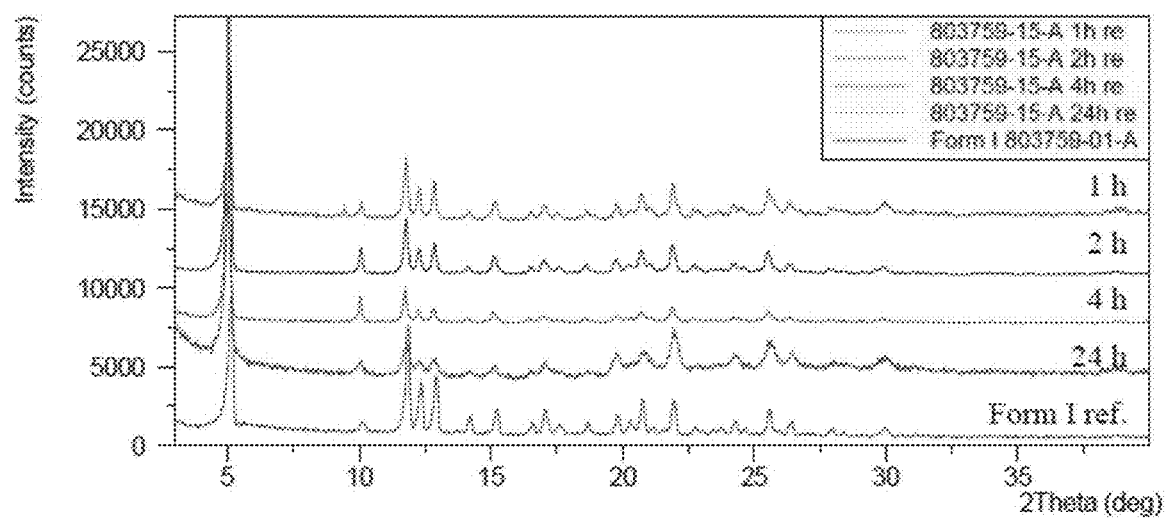
FIG. 14N shows XRPD patterns overlay of Form I sample milled at 5° C.
Figure 14O:
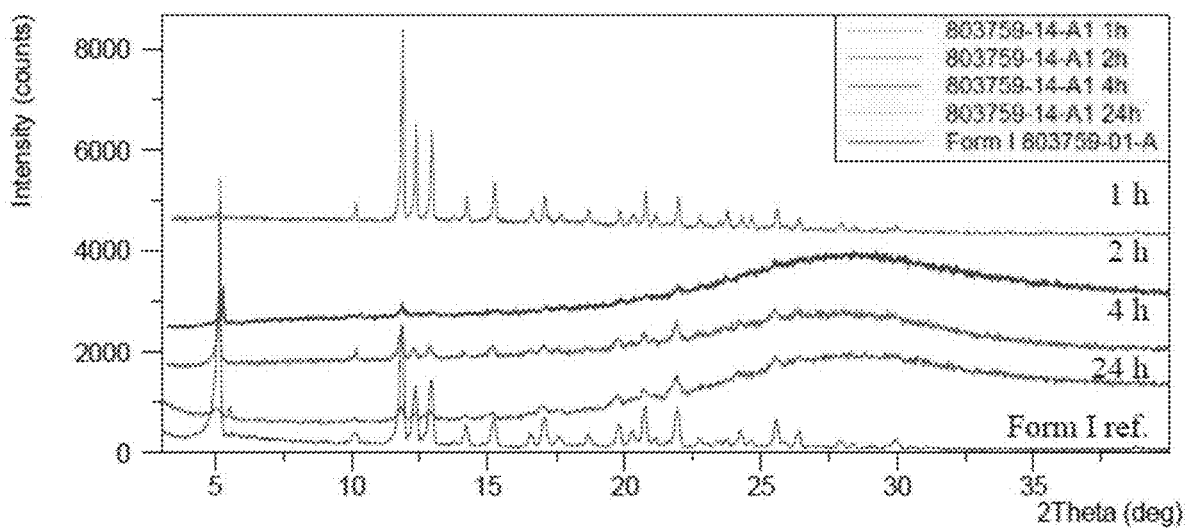
FIG. 14O shows XRPD patterns overlay of Form I sample milled at RT.
Figure 14P:
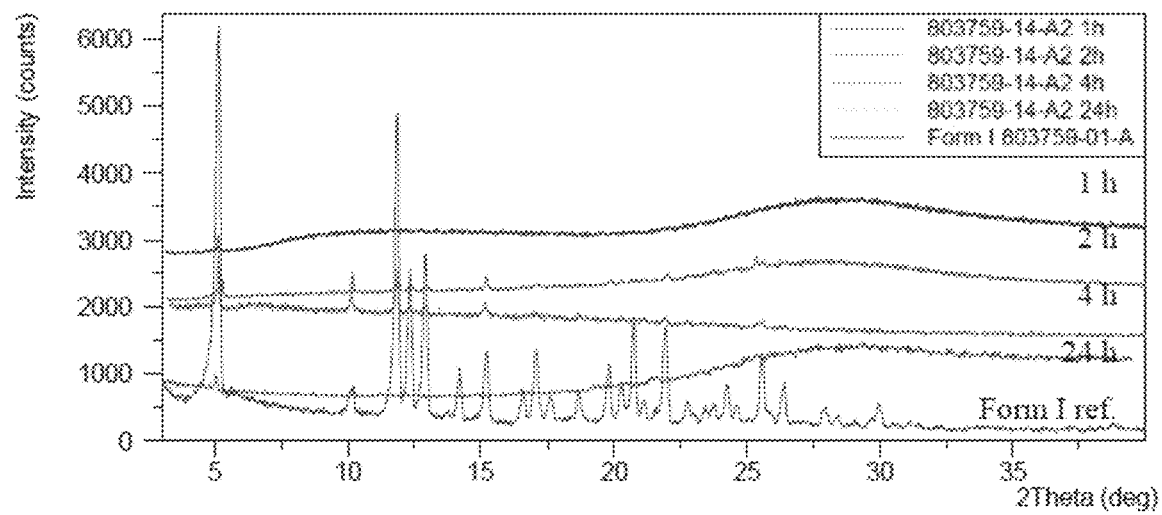
FIG. 14P shows XRPD patterns overlay of Form I sample milled at 60° C.
Figure 14R:
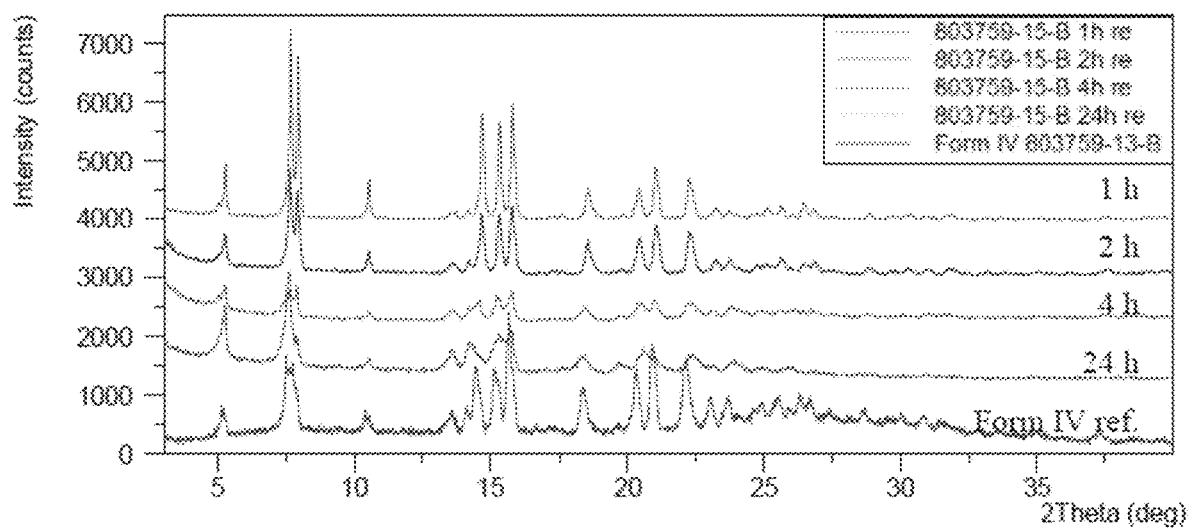
FIG. 14R shows XRPD patterns overlay of Form IV sample milled at 5° C.
Figure 14S:
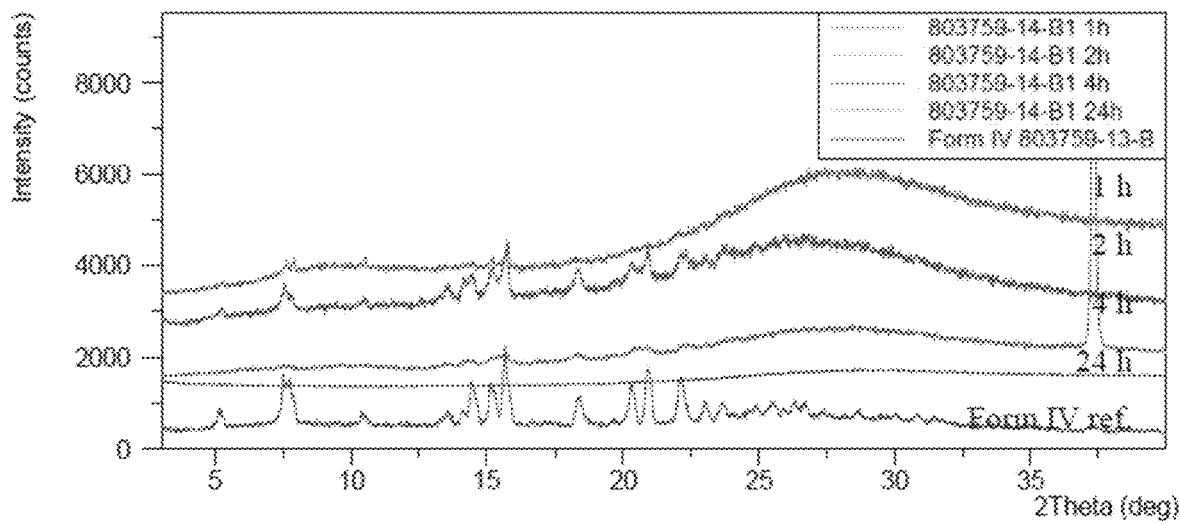
FIG. 14S shows XRPD patterns overlay of Form IV sample milled at RT.
Figure 14T:
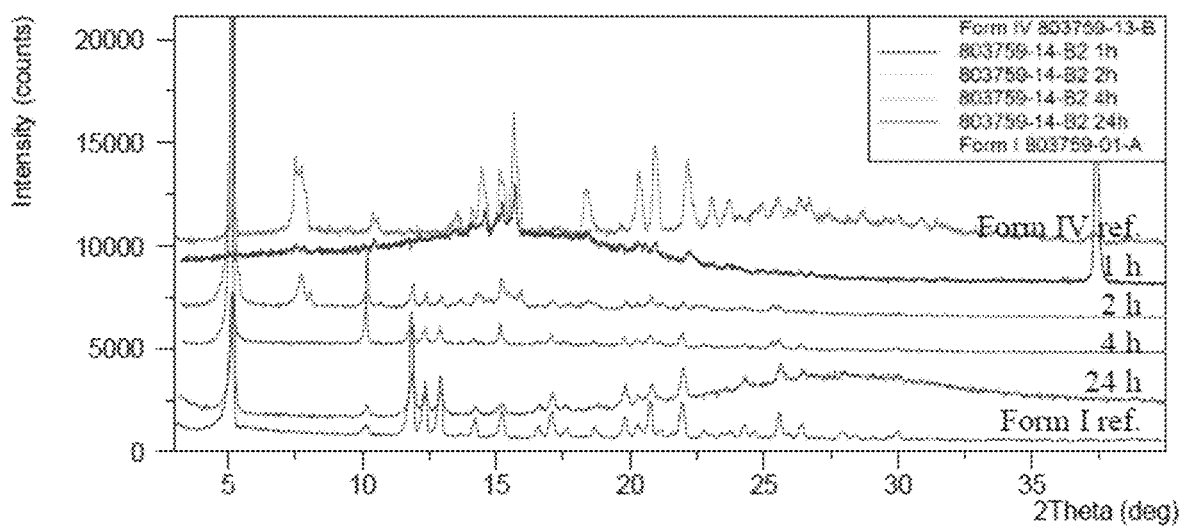
FIG. 14T shows XRPD patterns overlay of Form IV sample milled at 60° C.

The results displayed in Table 3 and in FIGS. 14A to 14T showed that:
1) form conversion was observed for Form IV at RT after 24 h and 60° C. after 2 h.
2) the particle size was decreased during milling.
3) Aggregation was observed for Form I at 5° C. and Form IV at 5° C. and RT after 24 h.

Therefore, ball milling of Form I sample at elevated temperature (60° C.) was recommended to reduce the particle size.

Additionally, the anticipated outcome is that milling of Form I at 60° C. or higher should prevent formation crystal seeds for the undesirable Form IV and result in a highly crystalline milled material that is annealed and free of high energy particles and free of amorphous material.

Ball milling of Form IV at elevated temperature (60° C.) confirmed conversion to Form I.

TABLE 3

Summary of ball milling for Form I and Form IV at different temperatures

| Experiment ID | | 803759-15-A | 803759-14-A1 | 803759-14-A2 |
|---|---|---|---|---|
| Initial Form | | | Form 1 | |
| Temperature, ° C. | | 5 | RT | 60 |
| 1 h | Form | Form I | Form I | Form I |
| | D 90 (μm) | 9.4 | 22.4 | 22.6 |
| 2 h | Form | Form I | Form I | Form I |
| | D 90 (μm) | 9.0 | 21.4 | 6.6 |
| 4 h | Form | Form I | Form I | Form I |
| | D 90 (μm) | 5.2 | 14.2 | 5.3 |
| 24 h | Form | Form I | Form I | Form I |
| | D 90 (μm) | 5.6 | 2.8 | 2.0 |

| Experiment ID | | 803759-15-B | 803759-14-B1 | 803759-14-B2 |
|---|---|---|---|---|
| Initial Form | | | Form IV | |
| Temperature, ° C. | | 5 | RT | 60 |
| 1 h | Form | Form IV | Form IV | Form IV |
| | D 90 (μm) | 33.7 | 6.6 | 3.9 |
| 2 h | Form | Form IV | Form IV | Form I + IV |
| | D 90 (μm) | 17.4 | 4.0 | 4.0 |
| 4 h | Form | Form IV | Form IV | Form I |
| | D 90 (μm) | 5.8 | 3.4 | 2.0 |
| 24 h | Form | Form IV | Amorphous | Form I |
| | D 90 (μm) | 9.8 | 5.8 | 0.6 |

To summarize, five crystal forms and amorphous sample of tegavivint were obtained. The summary is displayed in Table 4.

TABLE 4

Summary of tegavivint polymorphs

| Polymorph (ID) | Weight Loss (%) | Endotherm (° C., onset) | Form |
|---|---|---|---|
| Form I (803759-01-A) | 0.4 (150) | ND | Anhydrate |
| Form III (803759-05-A1) | 8.2 (100) | 64.5, 158.6* | Unidentified |
| Form IV (803759-13-B) | 8.4 (100) | 115.9#, 147.1* | Hydrate |
| Form V (803759-03-A 22 Apr) | NA | NA | Unidentified |
| Form VI (803759-02-B_N2back_30.0° C.) | NA | NA | Anhydrate |
| Amorphous (803759-04-B3 dry) | NA | 65.0** | Amorphous |

ND: no thermal event was observed before decomposition.
*exothermic peak.
peak temperature.
**glass transition temperature (middle temperature).
NA: the data was not collected

APPENDIX

Instruments and Methods

XRPD

For XRPD analysis, PANalytical X'Pert³ X-ray powder diffractometer was used. The XRPD parameters used are listed in Table 5.

TABLE 5

| Parameters for XRPD test | |
|---|---|
| Parameters | X' Pert# (reflection mode) |
| X-Ray | Cu, Kα, Kα1 (Å): 1.540598: Kα2 (Å): 1.544426 Kα2/Kα1 intensity ration: 0.50 |
| X-Ray tube setting | 45 KV, 40 mA |
| Divergence slit | 1/8° |
| Scan mode | Continuous |
| Scan range (°2Theta) | 3°~40° |
| Scan step time (s) | 46.667 |
| Step size (°2Theta) | 0.0263° |
| Test time (min) | ~5 min |

TGA, DSC and mDSC

TGA data were collected using a TA Discovery 5500/Q5000 TGA from TA Instruments. DSC and mDSC were performed using a TA Discovery 2500 DSC from TA Instruments. Detailed parameters used are listed in Table 6 and Table 7.

TABLE 6

| Parameters for TGA and DSC test | | |
|---|---|---|
| Parameters | TGA | DSC |
| Method | Ramp | Ramp |
| Sample pan | Aluminum, open | Aluminum crimped |
| Temperature | RT~350° C. | 25~300° C. |
| Heating rate | 10° C./min | 10° C./min |
| Purge gas | $N_2$ | $N_2$ |

TABLE 7

| Parameters for mDSC test | |
|---|---|
| Parameters | mDSC |
| Method | Conventional |
| Sample pan | Aluminum crimped |
| Temperature | 25~200° C. |
| Period | 60 s |
| Heating rate | 3° C./min |
| Purge gas | $N_2$ |

DVS

DVS was measured via a SMS (Surface Measurement Systems) DVS Intrinsic. The relative humidity at 25° C. were calibrated against deliquescence point of LiCl, $Mg(NO_3)_2$ and KCl. Parameters for DVS test were listed in Table 8.

TABLE 8

| Parameters for DVS test | |
|---|---|
| Parameters | DVS |
| Temperature | 25° C. |
| Sample size | 10~20 mg |
| Gas and flow rate | $N_2$, 200 mL/min |
| dm/dr | 0.002%/min |
| Min. dm/dt stability duration | 10 min |
| Max. equilibrium time | 180 min |
| RH range | 0% RH to 95% RH |
| RH step size | 10% RH from 0% RH to 95% RH 5% RH from 95% RH to 0% RH |

PLM

PLM images were captured using Axio Scope A1 microscope from Carl Zeiss German.

PSD

Microtrac S3500 with SDC (Sample Delivery Controller) was used for PSD test and the method is shown in Table 9.

TABLE 9

| PSD Method | |
|---|---|
| Parameters/Values | Parameters/Values |
| Distriction: Volume | Runtime: 10 sections/run |
| Dispersive solvent: water | Particle size coordinate: Standard |
| Run number: 3 runs, average | Solvent refractive index: 1.33 |
| Transparency: Trans | Residuals: Enabled |
| Particle refractive index: 1.59 | Flow rate: 60%* |
| Particle Shape: Irregular | Filter: On |
| Sonication power: NA | Sonication time: NA |

*60% of the maximum flow rate (65 mL/s)

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A crystalline form of a compound having the following formula:

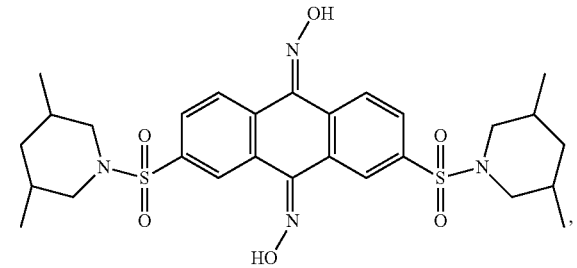 [SMILES: CC1CC(C)CN(S(=O)(=O)c2ccc3c(c2)C(=NO)c2cc(S(=O)(=O)N4CC(C)CC(C)C4)ccc2C3=NO)C1]

wherein the crystalline form is designated as Form IV and is characterized by having an endotherm before decomposition as shown by differential scanning calorimetry (DSC), wherein the endotherm has a peak maximum at about 115.9° C.

2. The crystalline form according to claim 1, wherein Form IV has an x-ray powder diffraction (XRPD) pattern with diffraction peaks having °2θ angle values comprising 5.0±0.2°; 7.5±0.2°; 7.7±0.2°; 14.8±0.2°; 15.2±0.2°; 15.4±0.2°; 20.0±0.2°; and 22.2±0.2°.

3. The crystalline form according to claim 1, wherein Form IV has an XRPD pattern with diffraction peaks having °2θ angle values comprising 5.0±0.2°; 7.5±0.2°; 7.7±0.2°; 10.2±0.2°; 14.8±0.2°; 15.2±0.2°; 15.4±0.2°; 20.0±0.2°; and 22.2±0.2°.

4. The crystalline form according to claim 1, wherein Form IV has an XRPD pattern with diffraction peaks having °2θ angle values comprising 5.0±0.2°; 7.5±0.2°; 7.7±0.2°; 10.2±0.2°; 14.8±0.2°; 15.2±0.2°; 15.4±0.2°; 18.0±0.2°; 20.0±0.2°; and 22.2±0.2°.

5. The crystalline form according to claim 1, wherein Form IV has an XRPD pattern with diffraction peaks having °2θ angle values comprising 5.0±0.2°; 7.5±0.2°; 7.7±0.2°; 10.2±0.2°; 14.8±0.2°; 15.2±0.2°; 15.4±0.2°; 18.0±0.2°; 20.0±0.2°; 20.5±0.2°; and 22.2±0.2°.

6. The crystalline form according to claim 1, wherein Form IV has an XRPD pattern with diffraction peaks having °2θ angle values comprising 5.0±0.2°; 7.5±0.2°; 14.8±0.2°; 15.2±0.2°; 15.4±0.2°; 20.0±0.2°; and 22.2±0.2°.

7. The crystalline form according to claim 1, wherein Form IV has an XRPD pattern with diffraction peaks having °2θ angle values comprising 14.8±0.2°; 15.2±0.2°; and 15.4±0.2°.

8. The crystalline form according to claim 1, wherein Form IV is further characterized by having an exotherm before decomposition as shown by differential scanning calorimetry (DSC).

9. The crystalline form according to claim 8, wherein the exotherm has a peak onset at about 147.1° C.

10. A nanosuspension prepared by providing the crystalline form according to claim 1 as a starting material and milling the starting material at a temperature of about 60° C.

11. A pharmaceutical composition, comprising a therapeutically effective amount of the nanosuspension according to claim 10, and a pharmaceutically acceptable excipient and/or diluent.

12. A method for treating or ameliorating cancer or tumor metastasis in a mammal in need thereof comprising administering to said mammal an effective amount of the pharmaceutical composition according to claim 11.

13. The method of claim 12, wherein the cancer is acute myeloid leukemia (AML).

14. The crystalline form according to claim 1, wherein Form IV is further characterized by a weight loss of about 8.4% up to 150° C. as shown by thermogravimetric analysis (TGA).

15. The crystalline form according to claim 1, wherein Form IV is further characterized by a water uptake of about 9.1% at 25° C. and 80% relative humidity (RH) as shown by dynamic vapor sorption (DVS).

16. The crystalline form according to claim 1, wherein Form IV is further characterized by exothermic decomposition starting at about 280° C.

17. The crystalline form according to claim 1, wherein Form IV is a hydrate.

18. The crystalline form according to claim 1, wherein Form IV is a trihydrate.

19. The crystalline form according to claim 18, wherein the trihydrate dehydrates thermally with a half-point of dehydration at about 60° C.

20. The crystalline form according to claim 1, wherein the crystal morphology is needles.

* * * * *